United States Patent
Addison et al.

(10) Patent No.: US 10,568,767 B2
(45) Date of Patent: Feb. 25, 2020

(54) SILICONE WOUND DRESSING LAMINATE AND METHOD FOR MAKING THE SAME

(75) Inventors: Deborah Addison, Near Clampham (GB); Sally Stephens, Skipton (GB); Patrick Joseph Brosnan, West Yorkshire (GB)

(73) Assignee: KCI USA, INC., San Antonio, TX (US)

(*) Notice: Subject to any disclaimer, the term of this patent is extended or adjusted under 35 U.S.C. 154(b) by 537 days.

(21) Appl. No.: 13/982,650

(22) PCT Filed: Jan. 31, 2012

(86) PCT No.: PCT/GB2012/000099
§ 371 (c)(1),
(2), (4) Date: Nov. 13, 2013

(87) PCT Pub. No.: WO2012/104584
PCT Pub. Date: Aug. 9, 2012

(65) Prior Publication Data
US 2014/0058309 A1 Feb. 27, 2014

(30) Foreign Application Priority Data
Jan. 31, 2011 (GB) .................................. 1101662.3

(51) Int. Cl.
*A61F 13/00* (2006.01)
*A61F 13/02* (2006.01)

(52) U.S. Cl.
CPC .... *A61F 13/00029* (2013.01); *A61F 13/0203* (2013.01); *A61F 13/0213* (2013.01);
(Continued)

(58) Field of Classification Search
CPC .......... A61F 13/00029; A61F 13/00017; A61F 13/00042; A61F 13/00046;
(Continued)

(56) References Cited

U.S. PATENT DOCUMENTS

| 1,355,846 A | 10/1920 | Rannells |
| 2,547,758 A | 4/1951 | Kelling |

(Continued)

FOREIGN PATENT DOCUMENTS

| AU | 550575 B2 | 3/1986 |
| AU | 745271 B2 | 3/2002 |

(Continued)

OTHER PUBLICATIONS

EP Examination Report dated May 22, 2014 for EP.
(Continued)

*Primary Examiner* — Keri J Nelson
*Assistant Examiner* — Michelle J Lee
(74) *Attorney, Agent, or Firm* — Foley & Lardner LLP

(57) ABSTRACT

A method of making a wound dressing comprising the steps of: providing an apertured substrate layer; coating the substrate layer with a fluid silicone prepolymer composition; thermally partially curing said silicone prepolymer composition to form a partially cured silicone coating on the substrate; laminating the coated substrate layer to a base layer to form a laminate having said partially cured silicone coating in contact with a surface of the base layer; followed by exposing the laminate to ionizing radiation, to further cure the partially cured silicone coating and to bond the silicone coating to said surface of the base layer. The radiation cure results in strong bonding between the siliconized substrate and incompatible base layers such as polyurethane foams. Also provided are wound dressings obtainable by the process of the invention.

13 Claims, 15 Drawing Sheets

(52) U.S. Cl.
CPC ...... *A61F 13/0223* (2013.01); *A61F 13/0226* (2013.01); *A61F 2013/00659* (2013.01)

(58) Field of Classification Search
CPC .............................. A61F 13/00–00046; A61F 2013/00089–00357; A61F 13/02–0293; A61F 13/04–069; A61F 13/10–148; A61F 2013/00361–00651; A61F 2013/00655–00893; A61L 15/00; A61L 15/16; A61L 15/58; A61L 26/00; A61L 2420/00
USPC ........ 604/304, 307; 424/443, 445; 427/2.31; 602/41–43, 47, 52, 54
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,172,808 A | 3/1965 | Baumann et al. |
| 3,367,332 A | 2/1968 | Groves |
| 3,376,868 A | 4/1968 | Mondiadis |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,777,016 A | 12/1973 | Gilbert |
| 3,779,243 A | 12/1973 | Tussey et al. |
| 3,826,254 A | 7/1974 | Mellor |
| 3,852,823 A | 12/1974 | Jones |
| 3,903,882 A * | 9/1975 | Augurt ............... A61F 13/00038 128/DIG. 8 |
| 3,967,624 A | 7/1976 | Milnamow |
| 3,983,297 A | 9/1976 | Ono et al. |
| 4,060,081 A * | 11/1977 | Yannas ................... A61F 2/105 128/DIG. 8 |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,758,220 A | 7/1988 | Sundblom et al. |
| 4,787,888 A | 11/1988 | Fox |
| 4,826,494 A | 5/1989 | Richmond et al. |
| 4,832,008 A | 5/1989 | Gilman |
| 4,838,253 A * | 6/1989 | Brassington ...... A61F 13/00008 128/DIG. 21 |
| 4,838,883 A | 6/1989 | Matsuura |
| 4,840,187 A | 6/1989 | Brazier |
| 4,848,364 A | 7/1989 | Bosman |
| 4,863,449 A | 9/1989 | Therriault et al. |
| 4,871,611 A | 10/1989 | Lebel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,930,997 A | 6/1990 | Bennett |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Lang et al. |
| 4,996,128 A | 2/1991 | Aldecoa et al. |
| 5,010,883 A | 4/1991 | Rawlings et al. |
| 5,018,515 A | 5/1991 | Gilman |
| 5,028,597 A * | 7/1991 | Kodama ............. A61L 33/0029 128/DIG. 8 |
| 5,037,397 A | 8/1991 | Kalt et al. |
| 5,086,170 A | 2/1992 | Luheshi et al. |
| 5,092,323 A | 3/1992 | Riedel et al. |
| 5,092,858 A | 3/1992 | Benson et al. |
| 5,100,396 A | 3/1992 | Zamierowski |
| 5,112,323 A | 5/1992 | Winkler et al. |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,261,893 A | 11/1993 | Zamierowski |
| 5,266,372 A | 11/1993 | Arakawa et al. |
| 5,270,358 A | 12/1993 | Asmus |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,356,386 A | 10/1994 | Goldberg et al. |
| 5,358,494 A | 10/1994 | Svedman |
| 5,384,174 A | 1/1995 | Ward et al. |
| 5,387,207 A | 2/1995 | Dyer et al. |
| 5,419,769 A | 5/1995 | Devlin et al. |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,501,212 A | 3/1996 | Psaros |
| 5,522,808 A | 6/1996 | Skalla |

(56) References Cited

U.S. PATENT DOCUMENTS

| | | |
|---|---|---|
| 5,527,293 A | 6/1996 | Zamierowski |
| 5,549,584 A | 8/1996 | Gross |
| 5,549,585 A | 8/1996 | Maher et al. |
| 5,556,375 A | 9/1996 | Ewall |
| 5,585,178 A | 12/1996 | Calhoun et al. |
| 5,599,292 A | 2/1997 | Yoon |
| 5,607,388 A | 3/1997 | Ewall |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,776,119 A | 7/1998 | Bilbo et al. |
| 5,807,295 A | 9/1998 | Hutcheon et al. |
| 5,919,476 A | 7/1999 | Fischer et al. |
| 5,941,863 A | 8/1999 | Guidotti et al. |
| 5,981,822 A | 11/1999 | Addison |
| 5,998,561 A * | 12/1999 | Jada .......... A61K 6/10 525/109 |
| 6,071,267 A | 6/2000 | Zamierowski |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 8,298,197 B2 | 10/2012 | Eriksson et al. |
| 8,529,532 B2 | 9/2013 | Pinto et al. |
| 8,632,523 B2 | 1/2014 | Eriksson et al. |
| 8,764,732 B2 | 7/2014 | Hartwell |
| 9,192,444 B2 | 11/2015 | Locke et al. |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0138604 A1 * | 7/2004 | Sigurjonsson .......... A61F 13/02 602/48 |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0159695 A1 * | 7/2005 | Cullen ............ A61L 15/28 602/48 |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0079852 A1 | 4/2006 | Bubb et al. |
| 2006/0083776 A1 | 4/2006 | Bott et al. |
| 2006/0154546 A1 | 7/2006 | Murphy et al. |
| 2006/0241542 A1 * | 10/2006 | Gudnason ............ A61F 13/0203 602/59 |
| 2006/0271020 A1 | 11/2006 | Huang et al. |
| 2007/0027414 A1 | 2/2007 | Hoffman et al. |
| 2007/0078366 A1 | 4/2007 | Haggstrom et al. |
| 2007/0185426 A1 | 8/2007 | Ambrosio et al. |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2008/0090085 A1 | 4/2008 | Kawate et al. |
| 2008/0119802 A1 | 5/2008 | Riesinger |
| 2008/0149104 A1 | 6/2008 | Eifler |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216204 A1 | 8/2009 | Bhavaraju et al. |
| 2009/0227969 A1 | 9/2009 | Jaeb et al. |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326488 A1 | 12/2009 | Budig et al. |
| 2010/0063467 A1 | 3/2010 | Addison et al. |
| 2010/0106106 A1 | 4/2010 | Heaton et al. |

(56) References Cited

U.S. PATENT DOCUMENTS

| | | | |
|---|---|---|---|
| 2010/0106118 A1 | 4/2010 | Heaton et al. |
| 2010/0125259 A1 | 5/2010 | Olson |
| 2010/0159192 A1 | 6/2010 | Cotton |
| 2010/0185163 A1 | 7/2010 | Heagle |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0305490 A1 | 12/2010 | Coulthard et al. |
| 2010/0305524 A1 | 12/2010 | Vess et al. |
| 2010/0324516 A1 | 12/2010 | Braga et al. |
| 2011/0046585 A1 | 2/2011 | Weston |
| 2011/0137271 A1 | 6/2011 | Andresen et al. |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0224631 A1 | 9/2011 | Simmons et al. |
| 2011/0229688 A1 | 9/2011 | Cotton |
| 2011/0244010 A1 * | 10/2011 | Doshi ............... A61K 9/0051 424/402 |
| 2011/0257617 A1 | 10/2011 | Franklin |
| 2012/0016322 A1 | 1/2012 | Coulthard et al. |
| 2012/0123359 A1 | 5/2012 | Reed |
| 2012/0143157 A1 | 6/2012 | Riesinger |
| 2012/0258271 A1 | 10/2012 | Maughan |
| 2013/0030394 A1 | 1/2013 | Locke et al. |
| 2013/0066285 A1 | 3/2013 | Locke et al. |
| 2013/0096518 A1 | 4/2013 | Hall et al. |
| 2013/0152945 A1 | 6/2013 | Locke et al. |
| 2013/0165837 A1 * | 6/2013 | Addison ............... A61L 15/26 602/44 |
| 2014/0039423 A1 | 2/2014 | Riesinger |
| 2014/0039424 A1 | 2/2014 | Locke |
| 2014/0155849 A1 | 6/2014 | Heaton et al. |
| 2014/0171851 A1 | 6/2014 | Addison |
| 2014/0309574 A1 | 10/2014 | Cotton |
| 2014/0350494 A1 | 11/2014 | Hartwell et al. |
| 2015/0030848 A1 | 1/2015 | Goubard |
| 2015/0119830 A1 | 4/2015 | Luckemeyer et al. |
| 2015/0190286 A1 | 7/2015 | Allen et al. |
| 2016/0067107 A1 | 3/2016 | Cotton |

FOREIGN PATENT DOCUMENTS

| | | |
|---|---|---|
| AU | 755496 B2 | 12/2002 |
| AU | 2009200608 A1 | 10/2009 |
| CA | 2005436 A1 | 6/1990 |
| CN | 87101823 A * | 8/1988 |
| DE | 26 40 413 A1 | 3/1978 |
| DE | 43 06 478 A1 | 9/1994 |
| DE | 29 504 378 U1 | 9/1995 |
| DE | 202004018245 U1 | 7/2005 |
| EP | 097517 A1 | 1/1984 |
| EP | 0100148 A1 | 2/1984 |
| EP | 0117632 A2 | 9/1984 |
| EP | 0147119 A2 | 7/1985 |
| EP | 0161865 A2 | 11/1985 |
| EP | 0275353 A2 | 7/1988 |
| EP | 0358302 A2 | 3/1990 |
| EP | 0538917 A1 | 4/1993 |
| EP | 0630629 A1 | 12/1994 |
| EP | 0659390 A2 | 6/1995 |
| EP | 0633758 B1 * | 10/1996 |
| EP | 0 251 810 A2 | 1/1998 |
| EP | 1 002 846 A1 | 5/2000 |
| EP | 1018967 A1 | 7/2000 |
| EP | 2578193 A1 | 4/2013 |
| GB | 692578 A | 6/1953 |
| GB | 1386800 A | 3/1975 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| GB | 2496310 A | 5/2013 |
| JP | 1961003393 | 2/1961 |
| JP | S62139523 U | 9/1987 |
| JP | S62-275456 A | 11/1987 |
| JP | 2007254515 A | 10/2007 |
| JP | 2008080137 A | 4/2008 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 8707164 A1 | 12/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 9622753 A1 | 8/1996 |
| WO | 97/18007 A1 | 5/1997 |
| WO | 99/13793 A1 | 3/1999 |
| WO | 99/65542 A1 | 12/1999 |
| WO | 01019306 A1 | 3/2001 |
| WO | 01/36188 A1 | 5/2001 |
| WO | 01/60296 A1 | 8/2001 |
| WO | 0168021 A1 | 9/2001 |
| WO | 0185248 | 11/2001 |
| WO | 0185248 A1 | 11/2001 |
| WO | 01085248 A1 | 11/2001 |
| WO | 0243743 A1 | 6/2002 |
| WO | 02062403 A1 | 8/2002 |
| WO | 03-018098 A2 | 3/2003 |
| WO | 03045294 A1 | 6/2003 |
| WO | 03045492 A1 | 6/2003 |
| WO | 03053484 A1 | 7/2003 |
| WO | 2004024197 A1 | 3/2004 |
| WO | 2004037334 A1 | 5/2004 |
| WO | 2004112852 A1 | 12/2004 |
| WO | 2005002483 A2 | 1/2005 |
| WO | 2005062896 A2 | 7/2005 |
| WO | 2005105176 A1 | 11/2005 |
| WO | 2005123170 A1 | 12/2005 |
| WO | 2007022097 A2 | 2/2007 |
| WO | 2007030601 A2 | 3/2007 |
| WO | 2007070269 A1 | 6/2007 |
| WO | 2007085396 A1 | 8/2007 |
| WO | 2007087811 A1 | 8/2007 |
| WO | 2007113597 A2 | 10/2007 |
| WO | 2007133618 A2 | 11/2007 |
| WO | 2008041926 A1 | 4/2008 |
| WO | 2008054312 A1 | 5/2008 |
| WO | 2008/082444 A2 | 7/2008 |
| WO | 2008100440 A1 | 8/2008 |
| WO | 2008104609 A1 | 9/2008 |
| WO | 2008/131895 A1 | 11/2008 |
| WO | 2009/002260 A1 | 12/2008 |
| WO | 2008149107 A1 | 12/2008 |
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009/124100 A1 | 10/2009 |
| WO | 2009126103 A1 | 10/2009 |
| WO | 2010032728 A1 | 3/2010 |
| WO | 2010/056977 A2 | 5/2010 |
| WO | 2010129299 A2 | 11/2010 |
| WO | 2011008497 A2 | 1/2011 |
| WO | 2011/049562 A1 | 4/2011 |
| WO | 2011043786 A1 | 4/2011 |
| WO | 2011115908 A1 | 9/2011 |
| WO | 2011121127 A1 | 10/2011 |
| WO | 2011162862 A1 | 12/2011 |
| WO | 2012/112204 A1 | 8/2012 |
| WO | 2012104584 A1 | 8/2012 |
| WO | 2012140378 A1 | 10/2012 |
| WO | 2012143665 A1 | 10/2012 |
| WO | 2013009239 A1 | 1/2013 |

(56) References Cited

FOREIGN PATENT DOCUMENTS

| | | |
|---|---|---|
| WO | 2013090810 A1 | 6/2013 |
| WO | 2014039557 A1 | 3/2014 |
| WO | 2014/113253 A1 | 7/2014 |
| WO | 2014140608 A1 | 9/2014 |
| WO | 2014143488 A1 | 9/2014 |
| WO | 2015/065615 A1 | 5/2015 |
| WO | 2015130471 A1 | 9/2015 |

OTHER PUBLICATIONS

International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/US2012/069893 dated Apr. 8, 2013.
Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/the British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N. A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. E Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N. a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion for PCT/US2013/070070 dated Jan. 29, 2014.

(56) References Cited

OTHER PUBLICATIONS

International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
Partial Internationl Search Report dated Jul. 31, 2009; PCT Internationl Application No. PCT/US2009/036222.
International Search Report and Written opinion dated Dec. 15, 2009; PCT Internation Application No. PCT/US2009/036222.
International Search Report and Written Opinion dated Feb. 24, 2010; PCT/US2009/057182.
International Search Report and Written Opinion dated Jan. 5, 2010; PCT International Application No. PCT/US2009/057130.
Response filed Oct. 20, 2011 for U.S. Appl. No. 12/398,904.
Interview Summary dated Oct. 27, 2011 for U.S. Appl. No. 12/398,904.
Non-Final Office Action dated Jul. 20, 2011 for U.S. Appl. No. 12/398,904.
V.A. Solovev et al., Guidelines, The Method of Treatment of Immagure External Fistulas in the Upper Gastrointestinal Tract, editor-in-chief Prov. V.I. Parahonyak (S.M. Kirov Gorky State Medican Institute, Gorky, U.S.S.R. 1987) ("Solovev Guidelines").
V.A. Kuznetsov & N.a. Bagautdinov, "Vacuum and Vacuum-Sorption Treatement of Open Septic Wounds," in All-Union Conference on Wounds and Wound Infections: Presentation Abstracts, edited by B.M. Kostyuchenok et al. (Mosco, U.S.S.R. Oct. 28-29, 1986) pp. 91-92 ("Bagautdinov II").
V.A. A Solovev, Dissertation Abstract, Treatement and Prevention of Suture Failures after Gastric Resection (S.M. Kirov Gorky State Medical Institute, Gorky, U.S.S.R. 1998 ("Solovev Abstract").
NDP 1000 Negative Pressure Wound Terapy System, Kalypto Medical, pp. 1-4.
Partial International Search Report dated Jul. 31, 2009 for PCT International Application No. PCT/US2009/036217.
International Search Report and Written Opinion dated May 31, 2010 for PCT Application No. PCT/US2009/064364.
Examination report for AU2009221772 dated Apr. 4, 2013.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
International Search Report and Written Opinion dated Oct. 19, 2010; PCT International Application No. PCT/US2009/036217.
International Search Report and Written Opinion dated Feb. 24, 2010; PCT International Application No. PCT/US2009/057182.
NPD 1000 Negative Pressure Would Therapy System, Kalypto Medical, pp. 1-4.
Partial International Search Report dated Jul. 31, 2009; PCT Internationl Application No. PCT/US2009/036222.
Non-Final Rejection for U.S. Appl. No. 12/398,904 dated Mar. 14, 2012.
Response to Non-Final Rejection for U.S. Appl. No. 12/398,904, filed Jun. 4, 2012.
International Search Report and Written Opinion for PCT/US2014/061251 dated May 8, 2015.
International Search Report and Written Opinion for PCT/IB2013/060862 dated Jun. 26, 2014.
PCT International Search Report in corresponding International Application No. PCT/GB2012/000099 dated May 2, 2012 (4 pages).
International Search Report and Written Opinion for PCT/US2015/015493 dated May 4, 2015.
European Search Report for corresponding Application No. 15194949.2.
European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion dated Jun. 1, 2011 for PCT International Application No. PCT/US2011/028344.
European Search Report for EP 11714148.1, dated May 2, 2014.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
International Search Report and Written Opinion for corresponding PCT application PCT/US2016/051768 dated Dec. 15, 2016.
European Search Report for corresponding EP Application 171572787 dated Jun. 6, 2017.
International Search Report and Written Opinion for corresponding application PCT/US2016/031397, dated Aug. 8, 2016.
European Search Report for corresponding application 17167872.5, dated Aug. 14, 2017.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).
European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.

\* cited by examiner

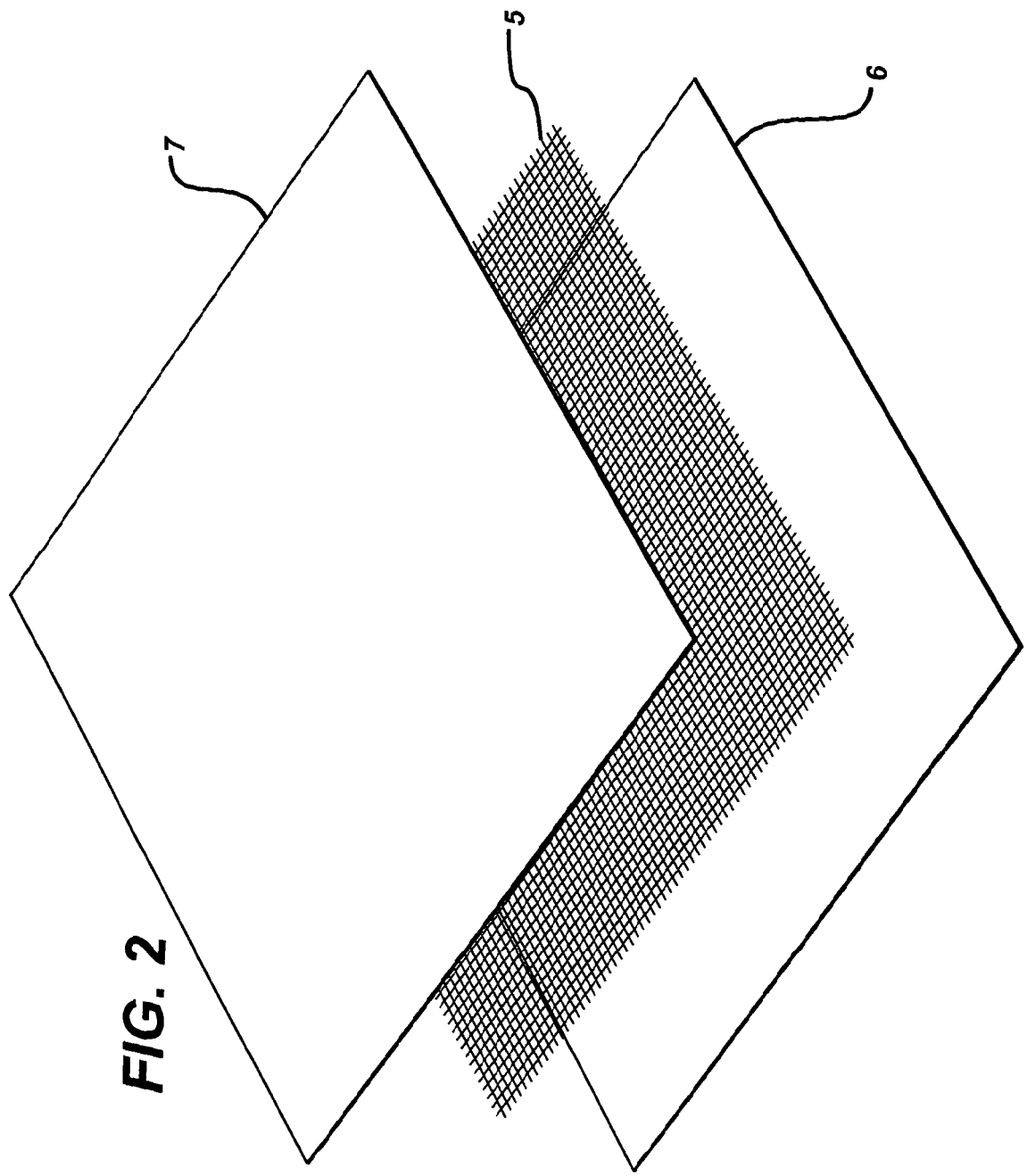

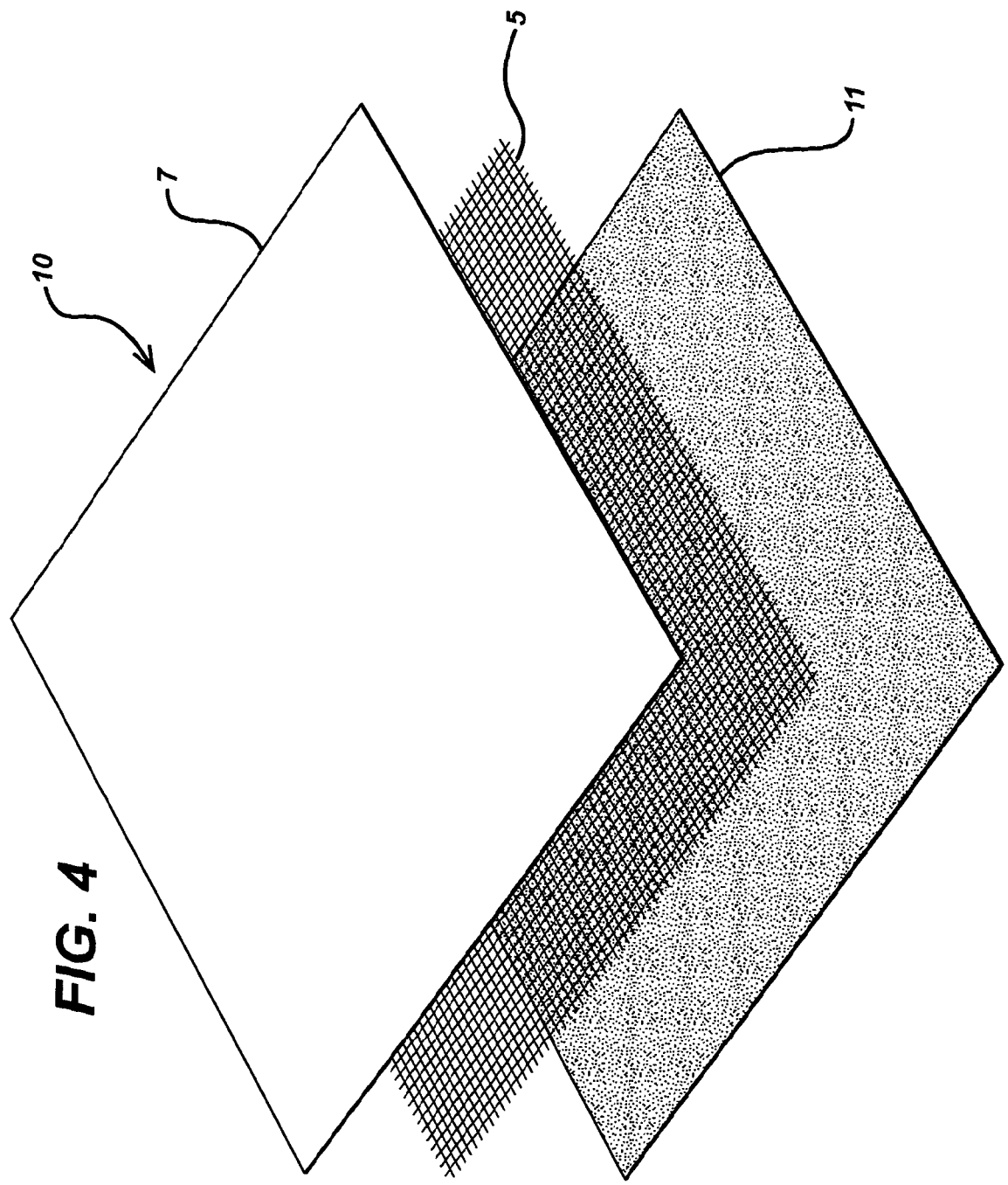

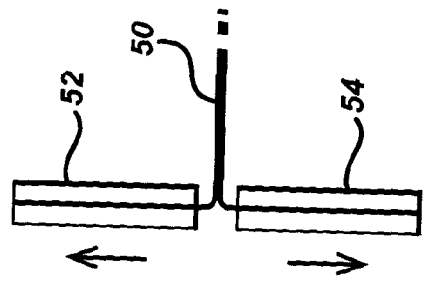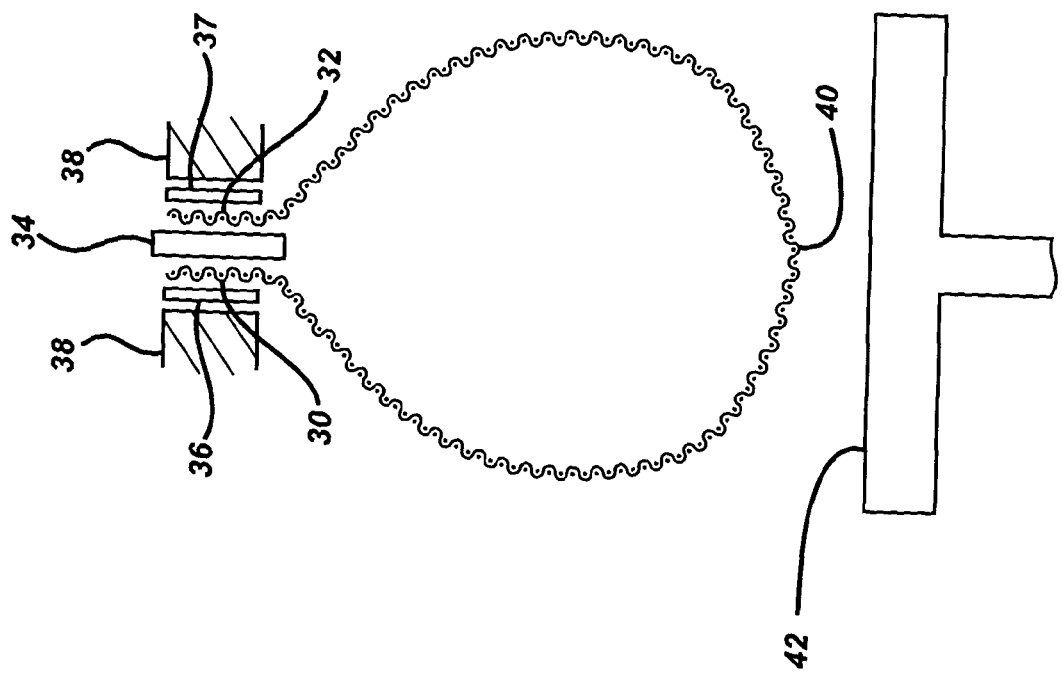

SILICONE WOUND DRESSING LAMINATE AND METHOD FOR MAKING THE SAME

The present invention relates to wound dressings comprising a laminate of a base layer and a silicone-coated layer, wherein the silicone-coated layer is bonded to the base layer. The invention also relates to methods of making such laminates.

Dressing materials for application to the surface of wounds should desirably be non-adherent to the moist wound surface. For this purpose a soft non-adherent or tacky (i.e. weakly adhesive) hydrophobic material is suitable for the wound contacting surface of the material. The wound contacting material should desirably be liquid-permeable to allow passage of wound fluid, especially for heavily exuding wounds such as burns. The material should also be non-irritating, inexpensive, and stable to common sterilization methods such as ionizing radiation.

Traditional "tulle gras" dressings generally consist of a layer of gauze coated with paraffin wax. Such dressings have a number of desirable properties, and for this reason have been used extensively for many years. Among these advantages are their high degree of conformability and deformability, and the fact that their tackiness makes them very easy to apply. That is to say, a tulle gras dressing applied to a wound will usually remain in place simply by adhesion of the paraffin wax to the patient's skin (or to itself in the case of a dressing wrapped around a finger, for example) while a securing bandage is applied. Tulle gras dressings are also quite inexpensive. However, tulle gras dressings do have a number of disadvantages. Principal amongst these is that, although initially non-adherent, they often become "dry" (in the sense of losing their paraffin coating) and consequently adhere to the wound to which they are applied. This effect is due to the paraffin coating becoming mobile at body temperatures and migrating into the wound or being absorbed into the backing of the dressing or bandage. In some cases, removal of a tulle gras dressing which has become dry in this way can cause considerable trauma. Indeed, it is quite common to have to soak tulle gras dressings in order to remove them. If tulle gras dressings are changed more frequently, in an attempt to avoid them becoming attached to the wound, this may delay wound healing and adds to nursing costs.

A further disadvantage of traditional tulle gras dressings is that fibres from the gauze may become incorporated in the wound, as may the paraffin coating of the dressing. Some authorities see the migration of paraffin into a wound as an undesirable effect and any paraffin found in a wound can be difficult to remove with normal aqueous wound cleansing agents. Moreover, the pores of the gauze may become occluded if the paraffin coating is too heavy or as a result of the mobility of the paraffin during use of the dressing. While occlusive dressings are appropriate in some circumstances, it is undesirable that the nursing staff should have no control over whether the dressing used is in fact occlusive.

Still further disadvantages of conventional tulle gras dressings are that they are effectively opaque and of somewhat unsightly appearance, and the paraffin can run during storage, making them particularly messy to apply.

EP-A-0251810 describes wound dressing s that overcome the above disadvantages by replacing the paraffin wax coating of conventional tulle gras by a tacky or non-tacky, hydrophobic silicone coating on a gauze or mesh substrate. In certain embodiments, the gauze may be provided with a tacky silicone coating on one side and a non-tacky silicone coating having a different composition on the other side. Similar materials are described in WO-A-8705206.

EP-A-0342950 describes similar wound dressings having a non-adherent silicone coating. The adherence of the silicone is reduced by addition of an amine-extended polyurethane.

WO-A-9319710 describes similar dressings further comprising a region of absorbent material laminated to the silicone-coated apertured substrate, and a fluid barrier layer behind the absorbent layer.

The above silicone-coated gauze dressings have achieved widespread use. However, a difficulty with the silicone-coated gauzes is that it can be difficult to laminate them securely to further dressing layers, such as a microorganism-impermeable semipermeable backing sheet or an absorbent layer. This is because the hydrophobic silicone is by its nature completely or substantially non-adherent. It would be desirable to make wound dressings having a laminated structure in which the apertured, silicone-coated wound contacting layer is securely bonded to one or more further layers, such as absorbent layers or continuous backing film layers.

WO-A-20100056544 describes gentle-to-skin silicone gel adhesives prepared by crosslinking a silicone prepolymer with electron beam or gamma radiation. The adhesives may be applied to suitable substrates before crosslinking.

The present inventors have found that normally non-adherent silicone-coated substrates can be strongly bonded to further wound dressing layers, such as absorbent layers or backing sheets, without the use of adhesives or silicone primer layers. This bonding is achieved by applying a silicone-coated layer wherein the silicone is incompletely cured to the further layer, followed by final curing of the silicone with ionizing radiation. The resulting laminates are useful as or in wound dressings.

In a first aspect, the present invention provides a wound dressing comprising: a base layer and an apertured layer laminated to the base layer, said apertured layer comprising an apertured substrate and a silicone coating layer on said substrate, wherein the apertured layer has been bonded to the base layer by ionizing radiation-induced bonding of the silicone coating to said base layer.

In a second aspect, the present invention provides a wound dressing comprising: a base layer and an apertured layer laminated to the base layer, said apertured layer comprising an apertured substrate and a silicone coating layer on said substrate, wherein the silicone coating is directly covalently bonded to the base layer.

In a third aspect, the present invention provides a wound dressing comprising: a base layer and an apertured layer laminated to the base layer, said apertured layer comprising an apertured substrate and a silicone coating layer on said substrate, wherein the apertured layer is directly bonded to the base layer and the peel strength required to separate the apertured layer from the base layer is greater than about 200 mN/cm, preferably greater than about 300 mN/cm, for example from about 400 mN/cm to about 1000 mN/cm.

In a further aspect, the invention provides a method of making a wound dressing comprising the steps of: providing an apertured substrate layer; coating the substrate layer with a fluid silicone prepolymer composition; thermally partially curing said silicone prepolymer composition to form a partially cured silicone coating on the substrate; laminating the coated substrate layer to a base layer to form a laminate having said partially cured silicone coating in contact with a surface of the base layer; followed by exposing the laminate to ionizing radiation, to further cure the partially cured silicone coating and to bond the silicone coating to said surface of the base layer.

It appears that the final cure with ionizing radiation results in chemical (e.g. covalent) bonding between the silicone and the base layer, thereby overcoming the normally non-adherent or weakly adherent nature of the silicone and resulting in a strong bond between the silicone and the base layer. It has been found that the use of certain silicone prepolymer formulations as described below is particularly advantageous for achieving an incomplete thermal cure that results in strong bonding of the silicone and the base layer in the final ionizing radiation treatment.

The term "wound dressing" herein refers primarily to products for topical application to wounds. However, it may encompass products for application to internal wounds. The products of the present invention may also be useful for application to intact skin, for example for transdermal administration of medicaments.

The base layer suitably provides a protective covering, cushioning, mechanical support and/or liquid absorbency to the wound dressing. Suitably, the base layer is formed from a material that is hydrophilic, suitably a material that does not swell or dissolve significantly in water or wound fluid. Suitably, the base layer is in the form of a sheet, for example a sheet having an uncompressed thickness of from about 0.2 mm to about 15 mm, for example from about 0.5 mm to about 5 mm.

The base layer may be any of the layers conventionally used to form layers over a wound contacting layer in a laminated wound dressing, for example absorbent layers or backing layers. In certain embodiments, the base layer is a backing layer in the form of a sheet of continuos semipermeable or impermeable polymer. In other embodiments the base layer may be an absorbent layer for example a hydrophilic foam, a sponge, a film, or a textile layer. The textile may be nonwoven, knitted or woven. In yet other embodiments the base layer may be a layer of pressure-sensitive adhesive, for example a layer of adhesive coated on a backing sheet. In these embodiments, the bonding between the silicone coating and the adhesive layer is stronger than would be expected simply from the effect of the adhesive, as will be explained further below.

The present invention achieves strong bonding between the silicone coating and base layer surfaces that are normally incompatible with and non-adherent to silicone, including hydrophilic surfaces such as polyurethane or hydrocolloid surfaces. This bonding is achieved without the use of a silicone primer to improve adhesion, i.e. it is direct bonding between the silicone and the material of the base layer.

In particular embodiments, the base layer is (a) a semipermeable or impermeable polymer film, or (b) a hydrophilic foam sheet, or (c) a nonwoven web.

Suitable semipermeable or impermeable polymer films for the base layer include any of the semipermeable films conventionally used to form a backing sheet of wound dressings. The films are suitably continuous, i.e. they do not comprise macroscopic apertures that would allow passage of wound fluid. Suitably, the base layer in these embodiments is also microorganism-impermeable. Suitable continuous conformable base layers of this type will suitably have a moisture vapor transmission rate (MVTR) of the base layer alone of 300 to 5000 $g/m^2/24$ hrs, suitably 500 to 2000 $g/m^2/24$ hrs at 37.5° C. at 100% to 10% relative humidity difference. It has been found that such moisture vapor transmission rates allow the wound under the dressing to heal under moist conditions without causing the skin surrounding the wound to macerate. The base layer thickness in these embodiments is suitably in the range of 10 to 1000 micrometers, more suitably 100 to 500 micrometers.

Suitable polymers for forming the base layer in these embodiments include polyurethanes and poly alkoxyalkyl acrylates and methacrylates. Suitably, the base layer in these embodiments comprises a continuous layer of a high density blocked polyurethane foam that is predominantly closed-cell. A suitable backing sheet material is the polyurethane film available under the Registered Trade Mark ESTANE 5714F.

Also suitable are elastomeric polymeric esters such as Du Pont HYTREL (Registered Trade Mark).

Suitable hydrophilic foam sheets for use as the base layer include polyurethane foams, carboxylated butadiene-styrene rubber, polyacrylate, polyvinylic or cellulosic foams. The hydrophilic foam may be open-cell or closed-cell. Suitably, the foam comprises a polyurethane, and more suitably it comprises at least 50% by weight of one or more polyurethanes, for example at least 75% by weight thereof.

The hydrophilic polyurethane foam materials are formed by reacting particular diisocyanates or isocyanate-capped prepolymers with suitable chain extending compounds having amine and/or alcohol multiple functionality. Chain terminating compounds such as mono-amines or monohydric alcohols may be included in the reaction mixture. Water may be included in the reaction mixture, since it reacts with isocyanate to liberate carbon dioxide for foaming the mixture.

The hydrophilic foams used in the base layers of the invention may also have the property of swelling and expanding when water is absorbed. The degree of swelling of the hydrophilic foams on complete saturation with an aqueous medium is typically at least 100% (expressed in terms of increase in volume), and suitably at least 200%. Preferred foams swell by 400 to 800%. Despite this high degree of swelling, however, the foams of the invention retain their integrity even after absorption of large quantities of water. Typically, the cells of the hydrophilic foams have an average diameter in the range 0.1 to 0.6 mm. Suitably hydrophilic foams are as described in EP-A-0541391. These foam layers are available from Systagenix Wound Management under the Registered Trade Marks TIELLE and HYPOL.

Suitably, the basis weight of the hydrophilic foam when used as a base layer in the materials of the present invention is from 0.2 to 1.5 $kg/m^2$, more suitably 0.5 to 1.0 $kg/m^2$.

Suitable textiles for use as the base layer include any of those conventionally used for absorbent products, including cellulose woven or nonwoven webs, or cellulose derivatives such as viscose, rayon or oxidized regenerated cellulose. In certain embodiments, the fabric comprises at least about 10 wt. % of hydrogel-forming absorbent fibers based on the dry weight of the fabric, for example, the fabric comprises at least about 20 wt. % of the hydrogel-forming fibers, for example from about 30 wt. % to about 50 wt. % of such fibers.

The term "hydrogel-forming fibers" refers to fibers that can absorb at least about twice their own weight of water, suitably at least about four times their own weight of water, to form a hydrogel. The fibers are normally insoluble in water. Suitable materials for the hydrogel-forming fibers include alginates, carboxymethylcelluloses, hydroxyethylcelluloses, polyacrylates, and hyaluronates. Suitable materials are calcium alginate and sodium carboxymethylcellulose and mixtures thereof.

Suitably, the fabric comprises at least about 10 wt. % based on the dry weight of the fabric of substantially non-water-absorbent textile fibers, and suitably it comprises at least about 20 wt. % of such fibers, for example from about 30 wt. % to about 60 wt. % of such fibers. Suitable non-absorbent textile fibers include polyamide fibers such as nylon fibers, polyolefin fibers, and viscose fibers.

Suitably, the absorbent layer is similar to those described in WO03/053584. That is to say, the absorbent layer comprises or consists essentially of a nonwoven fabric made up of a mixture of from about 10 wt. % to about 90 wt. % of hydrogel-forming absorbent fibers and from about 90 wt. % to about 10 wt. % of non-absorbent textile fibers. In certain embodiments, at least some of the non-absorbent textile fibers are coated with metallic silver)($Ag^0$) as an antimicrobial agent. Suitably, the amount of silver in the fabric is from about 0.1% to about 10 wt. %, based on the dry weight of the fabric. Textiles of this kind are available from Systagenix Wound Management under the Registered Trade Mark SILVERCEL.

The basis weight of the textile base layer may be in the range of 50-500 $g/m^2$, such as 100-400 $g/m^2$. The uncompressed thickness of the textile layer may be in the range of from 0.5 mm to 10 mm, such as 1 mm to 4 mm. The free (uncompressed) liquid absorbency measured for physiological saline may be in the range of 5 to 30 g/g at 25° C.

In embodiments, the base layer may be a layer of adhesive, in particular a pressure-sensitive adhesive. The base layer adhesive may be moisture vapor transmitting and/or patterned to allow passage of water vapor therethrough. The adhesive layer is suitably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane as described for example in GB-A-1280631. The basis weight of the adhesive layer is suitably 20 to 250 $g/m^2$, and more suitably 50 to 150 $g/m^2$. Polyurethane-based pressure sensitive adhesives are preferred.

In further embodiments, the base layer may comprise or consist of an odor absorbent textile, such as a charcoal cloth. GB-A-1301101 EP-A-0053936 and GB-A-2127389 describe activated carbon cloth for use as an odor absorbent wound dressing, for example in the treatment of heavily infected wounds, varicose ulcers and fungating carcinomas. The cloth is produced by carbonizing a cellulosic cloth, such as a suitably treated woven viscose rayon cloth. The activated carbon cloth is relatively friable, and tends to shed particles of carbon in use. For this reason it is preferably enclosed or covered by a suitable protective, permeable cover, such as a spunbonded nylon nonwoven or a gauze to prevent particles of carbon from escaping into the wound in use. Products of this type are commercially available under the Registered Trade Mark ACTISORB from Systagenix Wound Management. In these embodiments, the silicone coated substrate may be bonded directly to the charcoal cloth, or it may be bonded to a scrim enclosing the charcoal cloth.

In further embodiments, the base layer may comprise or consist of a second layer of the silicone coated apertured layer, which may be the same or different from the first layer of silicone coated apertured material. It has surprisingly been found that the methods of the present invention can achieve strong bonding between layers of apertured, silicone-coated materials. These embodiments allow the formation of envelopes of the silicone-coated substrate material having edges bonded together in face-to-face relation. The envelopes can contain any of the wound dressing materials described above, in sheet or particulate form.

The silicone coated substrate is apertured, whereby the substrate is permeable to wound fluid. For example, the substrate may be a mesh or web or fabric suitably formed from a woven, nonwoven or knitted textile, or it may be a molded mesh.

In certain embodiments the substrate is a fabric such as a gauze, or a mesh, having an array of apertures. The size and shape of the apertures in the substrate are not critical, but the apertures should suitably be such as to ensure that the material can be adequately coated with silicone gel without them becoming occluded. The apertures generally have an aspect ratio of from 1:1 to 5:1, and preferably from 1:1 to 2:1. For example, the apertures may be approximately circular or approximately square. The apertures suitably have an average diameter of from 0.3 to 4 mm, and more suitably from 0.5 to 2 mm.

The substrate is suitably formed from any medically acceptable material, such as cellulose, polyolefins, polyesters, or polyamides. An especially suitable material is cellulose acetate gauze. Substrates having a weight of from 15 to 200 $g/m^2$ are generally found to be suitable for use in the products of the invention, and fabrics weighing from 50 to 150 $g/m^2$ are most suitable. For example, certain embodiments employ a fabric of from 80 to 120 $g/m^2$.

Suitably, the silicone-coated substrate product retains open apertures to allow passage of wound fluid through the coated substrate. For example, an array of apertures may extend through said silicone coatings and the substrate layer. The open area of the coated substrate in the final product may for example be from about 1% to about 70%, for example from about 10% to about 50%.

Suitably, the substrate is coated on both sides with the silicone coating, so that the face of the substrate opposite the base layer presents a silicone surface to the wound. The wound facing silicone surface may be non-adherent, or it may be tacky.

For example, the tackiness of the wound facing surface as measured by a loop tack test (described below) is suitably from about 0.4N to about 2N, more suitably from about 0.5N to about 1.5N.

The total coating weight of the silicone on the substrate is suitably from about 50 $g/m^2$ to about 500 $g/m^2$, for example from about 80 $g/m^2$ to about 200 $g/m^2$, typically from about 100 $g/m^2$ to about 150 $g/m^2$. The silicone is suitably a soft skin adhesive silicone composition. Suitable chemistry is described below. The silicone is suitably hydrophobic.

The effectiveness of encapsulation by silicone means that the substrate may be printed or dyed with decorative or informative matter with little danger of the ink or dye being released into the wound to which the dressing is applied. Visible indicia, such a colour or writing, may be provided on the substrate.

The coated substrate is laminated to the base layer, and optionally to further layers, to form the wound dressings according to the invention. Some of the laminate structures falling within the scope of the invention are as follows:

Embodiment 1: An absorbent base layer in the form of a sheet of absorbent material (or adsorbent material, such as charcoal cloth) having upper and lower surfaces, and having the silicone-coated substrate bonded to at least one of the surfaces to provide a non-adherent wound-contacting surface. In certain embodiments, silicone-coated substrates are bonded to both surfaces to provide a dressing material that can be applied to the wound in either orientation.

Embodiment 2: a laminate according to Embodiment 1, further laminated to an adhesive-coated backing sheet to provide an absorbent dressing with a liquid-impermeable backing sheet. In these embodiments, the laminate is formed so that at least the wound facing surface of the absorbent layer opposite to the backing sheet is bonded to the silicone-coated substrate to provide a non-adherent wound contacting surface. Further layers, such as further absorbent layers, may be provided between the absorbent layer and the backing sheet.

Embodiment 3: Similar to Embodiment 2, but in the form of an island dressing such that the adhesive-coated backing sheet is larger than the absorbent layer whereby a margin of the backing sheet extends around the edges of the absorbent layer. In these embodiments, the silicone-coated substrate may be coterminous with the absorbent island, or it may extend beyond the edges of the island whereby a margin of the silicone-coated substrate is bonded to the backing sheet or to the adhesive coating on the backing sheet around the absorbent island.

Embodiment 4: This embodiment has the silicone-coated substrate directly bonded to a liquid-impermeable backing sheet, or to a layer of adhesive on the backing sheet, i.e. there is no absorbent layer. These embodiments are suitable for more lightly exuding wounds for which water vapour permeability through the semipermeable backing sheet is sufficient.

Embodiment 5: This embodiment has the silicone-coated substrate directly bonded to a liquid-impermeable backing sheet, or to a layer of adhesive on the backing sheet, and further comprising an absorbent layer or absorbent island over the silicone-coated substrate, i.e. the substrate is sandwiched between the absorbent layer and the base layer. In the case of island dressings, the substrate may extend to the edges of the backing sheet to provide a more skin-friendly surface to the margin of the dressing. A further layer of the silicone-coated substrate may be bonded to the wound facing surface of the absorbent layer or island.

Embodiment 6: Two pieces (or one folded piece) of silicone coated substrate encasing an absorbent or adsorbent layer such as charcoal cloth. The silicone coated substrate is larger than the absorbent/adsorbent layer whereby the substrate overlaps around the edges of the absorbent/adsorbent layer to form margins which are bonded together in face-to-face fashion to form an envelope of the silicone-coated substrate around the absorbent/adsorbent layer.

Suitably, the wound dressing according to the present invention comprises less than 10% water prior to use as an absorbent, more suitably less than 5% water and more suitably it contains less than 2% of water before use.

Suitably, the wound dressing according to the present invention has a maximum total uncompressed thickness of from about 0.2 mm to about 15 mm, for example from about 0.5 mm to about 5 mm. Suitably, the wound dressing according to the present invention is in the form of a piece having a total area of from about 1 $cm^2$ to about 1000 $cm^2$, for example from about 5 $cm^2$ to about 400 $cm^2$.

The dressing may comprise one or more releasable cover sheets over the wound facing surface of the substrate opposite to the base layer to protect the substrate surface before use. The cover sheets may comprise a film of polyethylene, polypropylene or fluorocarbons and papers coated with these materials. Suitably, the cover sheet is a release-coated paper sheet, such as a silicone release-coated paper sheet. Examples of silicone-coated release papers are POLYSLIK (Registered Trade Mark) supplied by H.P. Smith & Co., offered in various formulations to control the degree of adhesion of the paper to the silicone coated substrate surface.

In certain embodiments, the cover sheets may comprise two or more parts, such as a first removable part having a first edge and a second removable part that meets the first part along the first edge. Suitably, along each of said edges where the parts meet, one of the parts is folded back to provide a folded-back margin, and the other part overlaps the said folded-back margin. This provides an easy-to-grasp margin on each part in the region of overlap to assist removal of the cover sheet by the care giver. In other embodiments, the cover sheets may comprise three parts, for example as described in detail in EP-A-0117632.

Suitably, the wound dressings of the invention are sterile and packaged in a microorganism-impermeable container.

In a further aspect, the invention provides a method of making a wound dressing comprising the steps of: providing an apertured substrate layer; coating the substrate layer with a fluid silicone prepolymer composition; thermally partially curing said silicone prepolymer composition to form a partially cured silicone coating on the substrate; laminating the coated substrate layer to a base layer to form a laminate having said partially cured silicone coating in contact with a surface of the base layer; followed by exposing the laminate to ionizing radiation, to further cure the partially cured silicone coating and to bond the silicone coating to said surface of the base layer.

The substrate layer is suitably as previously described for the products of the invention. Suitably, the substrate layer is permeable to the fluid silicone prepolymer composition.

The step of coating may be performed in any conventional way, for example immersion, spraying, or doctor blade. The step of coating suitably comprises passing the coated substrate through nip rollers to ensure smooth coating and penetration of the coating composition. Suitably, the step of coating is followed by a step of blowing gas (such as air) through the substrate to ensure that the apertures in the material are open after coating.

The fluid silicone coating composition is suitably substantially or completely solvent-free. The methods of the present invention allow substrates having silicone coating on the upper and lower surfaces to be made with a single silicone coating composition on both surfaces.

Suitably, the silicone composition is a so-called soft skin adhesive silicone elastomer. Such silicones can be made by an addition reaction (hydrosilylation) between (a) a vinyl functional polydimethyl siloxane, such as bis-dimethyl vinyl PDMS, and (b) a hydrogen functional siloxane, such as dimethyl, methylhydrogen siloxane copolymers, hydrogen dimethylsiloxy terminated PDMS. The cure reaction is catalyzed by a hydrosilylation catalyst, such as a noble metal catalyst, suitably a platinum catalyst. Suitably the silicone prepolymer composition further comprises a polymerization inhibitor that is evaporated from said composition during said step of thermally partially curing, for example 2-methyl-3-butyn-2-ol. The polymerization inhibitor is suitably present in an amount of from about 0.001 wt. % to about 1 wt. %, for example from about 0.01 wt. % to about 0.1 wt. % before curing.

Silicone skin adhesive compositions are suitably supplied as two-part systems: Part A contains at least the vinyl prepolymer and the catalyst, while Part B contains the vinyl prepolymer and the SiH siloxane cross linker. The components are mixed immediately before use, optionally with addition of the polymerization inhibitor.

In embodiments, the silicone coating composition comprises or consists essentially of the following components:
(A) a diorganopolysiloxane having at least 2 alkenyl groups in each molecule;

(B) an organohydrogenpolysiloxane having at least 2 silicon-bonded hydrogen atoms in each molecule, in a quantity sufficient for the ratio between the number of moles of silicon-bonded hydrogen atoms in this component and the number of moles of alkenyl groups in component (A) to have a value of from about 0.6:1 to about 20:1, (C) optionally a platinum group metal catalyst suitably in a quantity providing 0.1 to 500 weight parts as platinum group metal per 1,000,000 weight parts component (A); and (D) a volatile polymerization inhibitor, suitably selected from: alkyne alcohols such as 2-methyl-3-butyn-2-ol, 3,5-dimethyl-1-hexyn-3-ol, and phenylbutynol; ene-yne compounds such as 3-methyl-3-penten-1-yne and 3,5-dimethyl-3-hexen-1-yne; tetramethyltetrahexenyl-cyclotetrasiloxane; and benzotriazole.

The diorganopolysiloxane, component (A), used in the instant invention is the base component of the total composition. This diorganopolysiloxane must contain at least 2 alkenyl groups in each molecule in order for this composition to cure into a rubbery elastic silicone rubber coating composition.

The diorganopolysiloxane (A) comprises essentially straight-chain organopolysiloxane with the average unit formula $R_nSiO_{(4-n)/2}$, wherein R is selected from substituted and unsubstituted monovalent hydrocarbon groups and n has a value of 1.9 to 2.1. R may be exemplified by alkyl groups such as methyl, ethyl, propyl, and others; alkenyl groups such as vinyl, allyl, and others; aryl groups such as phenyl, and others; and haloalkyl groups such as 3,3,3-trifluoropropyl and others. The diorganopolysiloxane (A) should have a viscosity at 25° C. of at least 100 centipoise (1 d Pa·s). When such factors as the strength of the silicone rubber coating membrane, and blendability are taken into account, the viscosity of diorganopolysiloxane (A) at 25° C. is preferably from 1,000 centipoise (1 Pa·s) to 100,000 centipoise (100 Pa·s). The diorganopolysiloxane (A) may be exemplified by dimethylvinylsiloxy-endblocked dimethylpolysiloxanes, dimethylvinylsiloxy-endblocked dimethylsiloxane-methylvinylsiloxane copolymers, and dimethylvinyl-siloxy-endblocked dimethylsiloxane-methylphenylsiloxane copolymers.

Component (B), an organopolysiloxane that contains at least 2 silicon-bonded hydrogen atoms in each molecule, is a crosslinker for the composition of the instant invention. The organopolysiloxane (B) may be exemplified by trimethylsiloxy-endblocked methyl-hydrogenpolysiloxanes, trimethylsiloxy-endblocked dimethylsiloxanemethylhydrogen-siloxane copolymers, dimethylphenylsiloxy-endblocked methylphenylsiloxanemethyl-hydrogensiloxane copolymers, cyclic methylhydrogenpolysiloxanes, and copolymers that contain the dimethylhydrogensiloxy unit and SiO4/2 unit. The organohydrogenpolysiloxane (B) should be added in a quantity that the ratio between the number of moles of silicon-bonded hydrogen atoms in this organohydrogenpolysiloxane and the number of moles of alkenyl groups in component (A) has a value of 0.6:1 to 20:1.

The platinum group metal catalyst, component (C), used in the compositions is a curing catalyst. The platinum group metal catalyst (C) may be exemplified by platinum micropowder, platinum black, chloroplatinic acid, platinum tetrachloride, olefin complexes of chloroplatinic acid, alcohol solutions of chloroplatinic acid, complexes between chloroplatinic acid and alkenylsiloxanes, rhodium compounds, and palladium compounds. The platinum group metal catalyst (C) should be added generally at 0.1 to 500 weight parts as platinum group metal per 1,000,000 weight parts component (A), and is preferably used at 1 to 50 weight parts as platinum group metal per 1,000,000 weight parts component (A). The reaction will not develop adequately at less than 0.1 weight parts, while additions in excess of 500 weight parts are uneconomical.

The coated substrate is then subjected to thermal curing to partially cure the silicone. The thermal coating is suitably performed continuously by passing the coated substrate through an oven. Suitable thermal curing conditions include exposure to a temperature of from about 80° C. to about 200° C., for example about 120° C. to about 180° C. for a time of from about 1 minute to about 10 minutes, for example about 1.5 minutes to about 5 minutes. The elevated temperature results in evaporation of the polymerization inhibitor from the silicone composition and therefore in polymerization of the silicone. The resulting material is chemically polymerized, but capable of further curing by ionizing radiation as explained further below. The partially thermally cured material is dimensionally stable, for example an elastomer or a gel, so that it can readily be laminated onto the base layer without substantial deformation.

The siliconized substrate is suitably laminated to the base layer after the step of thermal polymerizing since the silicone is no longer fluid at this stage so that handling is easier and the porosity of the substrate is preserved in the laminating step. The siliconized substrate is only weakly adhered to the base layer at this stage.

Suitably, the releasable cover sheet is applied over the surface of the substrate opposite the base layer also at this stage. In other embodiments, the releasable cover sheet is applied after the step of curing with ionizing radiation described below.

The partially cured material is then subjected to a final cure with ionizing radiation. The ionizing radiation is suitably selected from e-beam radiation and gamma radiation. A variety of procedures for E-beam and gamma ray curing are well-known. The cure depends on the specific equipment used, and those skilled in the art can define a dose calibration model for the specific equipment, geometry, and line speed, as well as other well understood process parameters.

Commercially available electron beam generating equipment is readily available. For example, a Model CB-300 electron beam generating apparatus (available from Energy Sciences, Inc. (Wilmington, Mass.). Generally, a support film (e.g., polyester terephthalate support film) runs through a chamber. Generally, the chamber is flushed with an inert gas, e.g., nitrogen while the samples are e-beam cured. Multiple passes through the e-beam sterilizer may be needed.

Commercially available gamma irradiation equipment includes equipment often used for gamma irradiation sterilization of products for medical applications. Cobalt 60 sources are appropriate. Total absorbed doses are suitably from 20 to 60 kGy, more suitably from about 35 to 50 kGy and dose rates are suitably about 7 to 8 kGy/hour.

The step of further curing with ionizing radiation is effective to bond the silicone surface of the substrate strongly to the surface of the base layer. This is thought to be due to the ionizing radiation forming covalent bonds between the silicone and the base layer material. The effect is seen also when the base layer is coated with a conventional pressure sensitive medical adhesive, such as a polyurethane-based pressure sensitive adhesive. In these cases, a bond is formed with the adhesive that has much higher peel strength than the bond formed with the adhesive before irradiation.

Suitably, the method comprises the step of packaging the material in a microorganism-impermeable container prior to the step of further curing with ionizing radiation, whereby the step of further curing also sterilizes the material.

The methods of the invention may be used to make any products according to the invention. Conversely, any of the products of the invention may be obtainable by a method according to the invention. Any feature disclosed herein in relation to any one or more aspects of the invention is suitable for use in any of the other aspects defined herein.

Specific embodiments of the invention will now be described further, by way of example, with reference to the accompanying drawings, in which:

FIG. 2 shows a perspective exploded view of a first product according to the invention;

FIG. 4 shows a perspective exploded view of a second product according to the invention;

FIG. 17 shows a schematic drawing of the loop tack test configuration used in Procedure 1 below; and FIG. 18 shows a schematic drawing of the peel strength test configuration used in Procedure 2 below.

Figure 1:
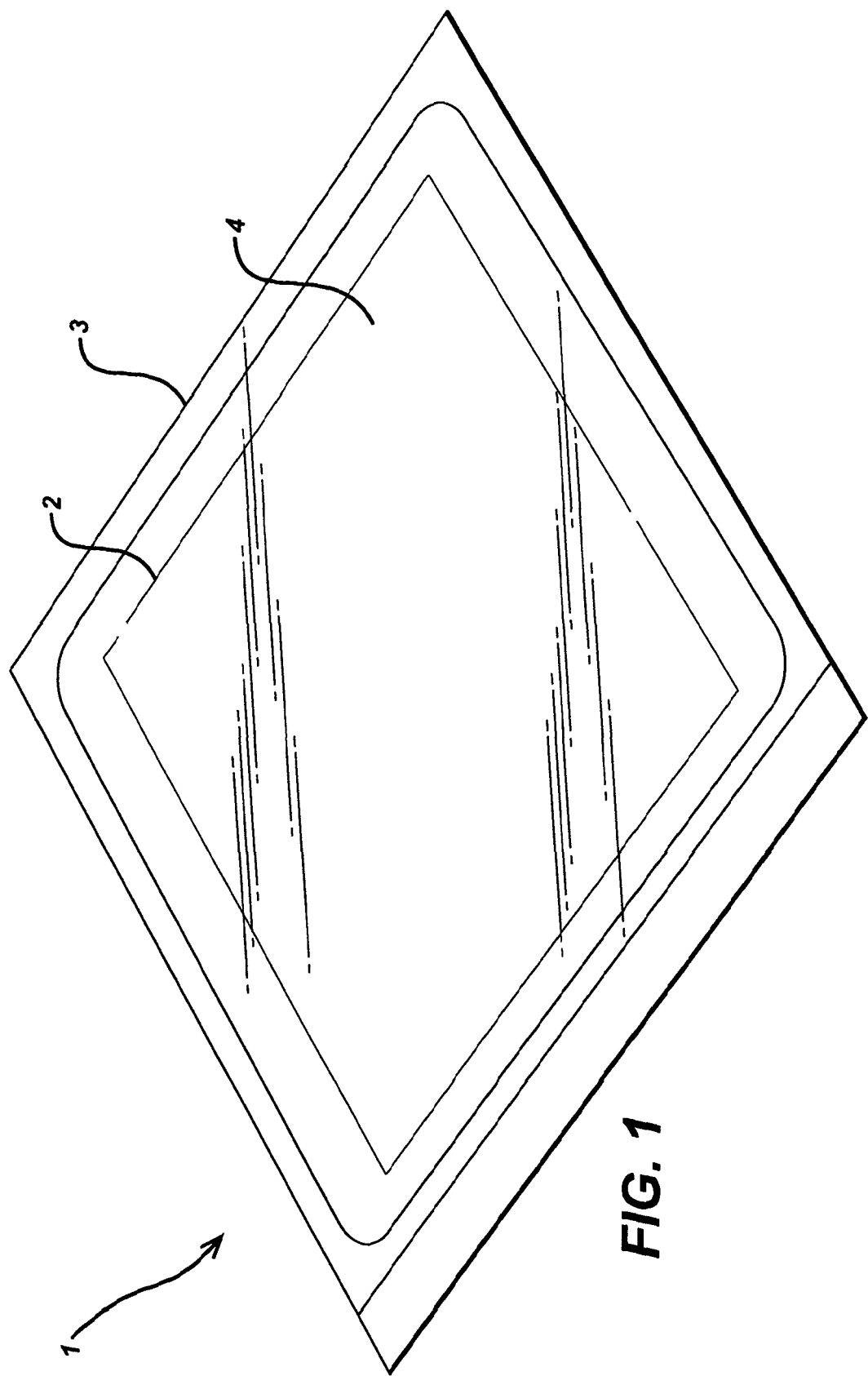
FIG. 1 shows a perspective view of a product according to the invention packaged in a microorganism-impermeable pouch.

Referring to FIG. 1, a packaged wound dressing 1 according to the invention is shown. The dressing 2 is sterile and packaged in a microorganism-impermeable envelope 3 of polypropylene or the like having a transparent window 4.

Figure 3:
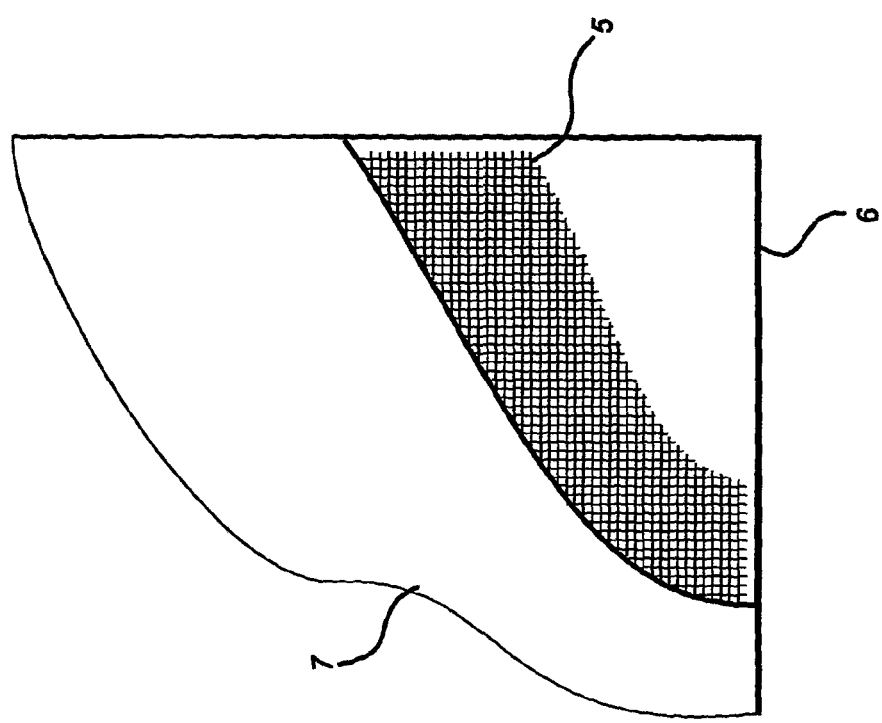
FIG. 3 shows a partially cut away view of part of the product of FIG. 2.

Referring to FIGS. 2 and 3, the siliconized substrate 5 in this and all of the other embodiments shown in the drawings comprises a substrate of cellulose acetate gauze of density 107 grams per square meter nominal, coated with a hydrophobic, tacky, crosslinked silicone gel, prepared as described below. The silicone composition penetrates the gauze to form a single, chemically homogeneous silicone phase coating the strands of the gauze. The coated substrate 5 has an array of apertures extending through the substrate and the silicone to allow passage of wound fluid through the material. The nominal total coating weight of the silicone is 120-130 grams per square meter.

The upper siliconized surface is bonded to a base layer 6, which in this embodiment is a semipermeable microporous polyurethane backing layer, which may or may not be coated with a polyurethane pressure-sensitive adhesive layer. The opposite surface of the siliconized substrate is covered by a release sheet 7 of siliconized paper that can be peeled off to expose the siliconized surface for application to a wound or to skin.

Figure 5:
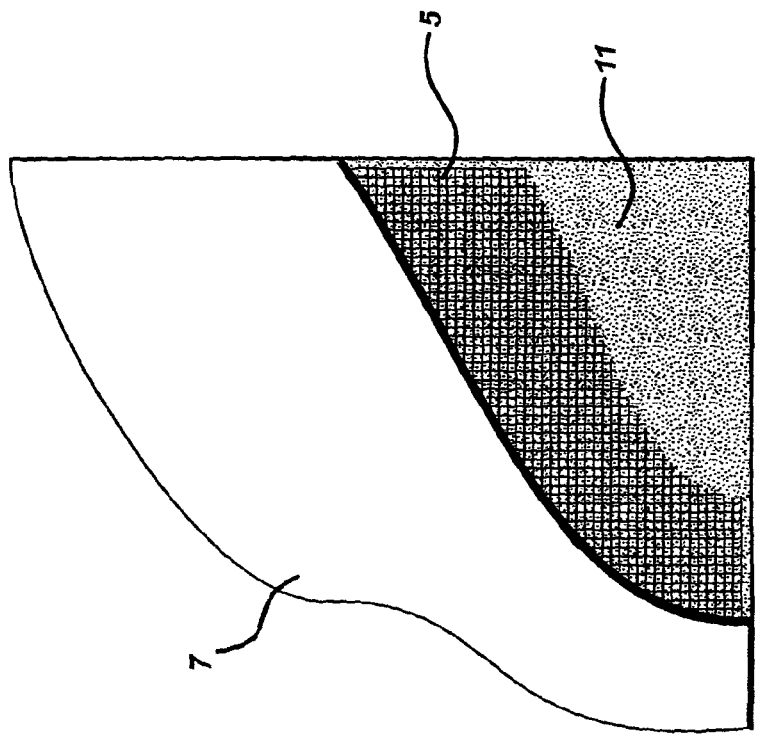
FIG. 5 shows a partially cut away view of part of the product of FIG. 4.

Referring to FIGS. 4 and 5, the product 10 according to this embodiment comprises a siliconized substrate gauze 5 and releasable cover sheet 7 as before, but in this embodiment the base layer 11 is a sheet of water-absorbent hydrophilic polyurethane foam prepared as described in EP-A-0541391. The foam can absorb wound fluid and swell in use, while remaining strongly bonded to the siliconized gauze wound contacting layer 5.

Figure 6:
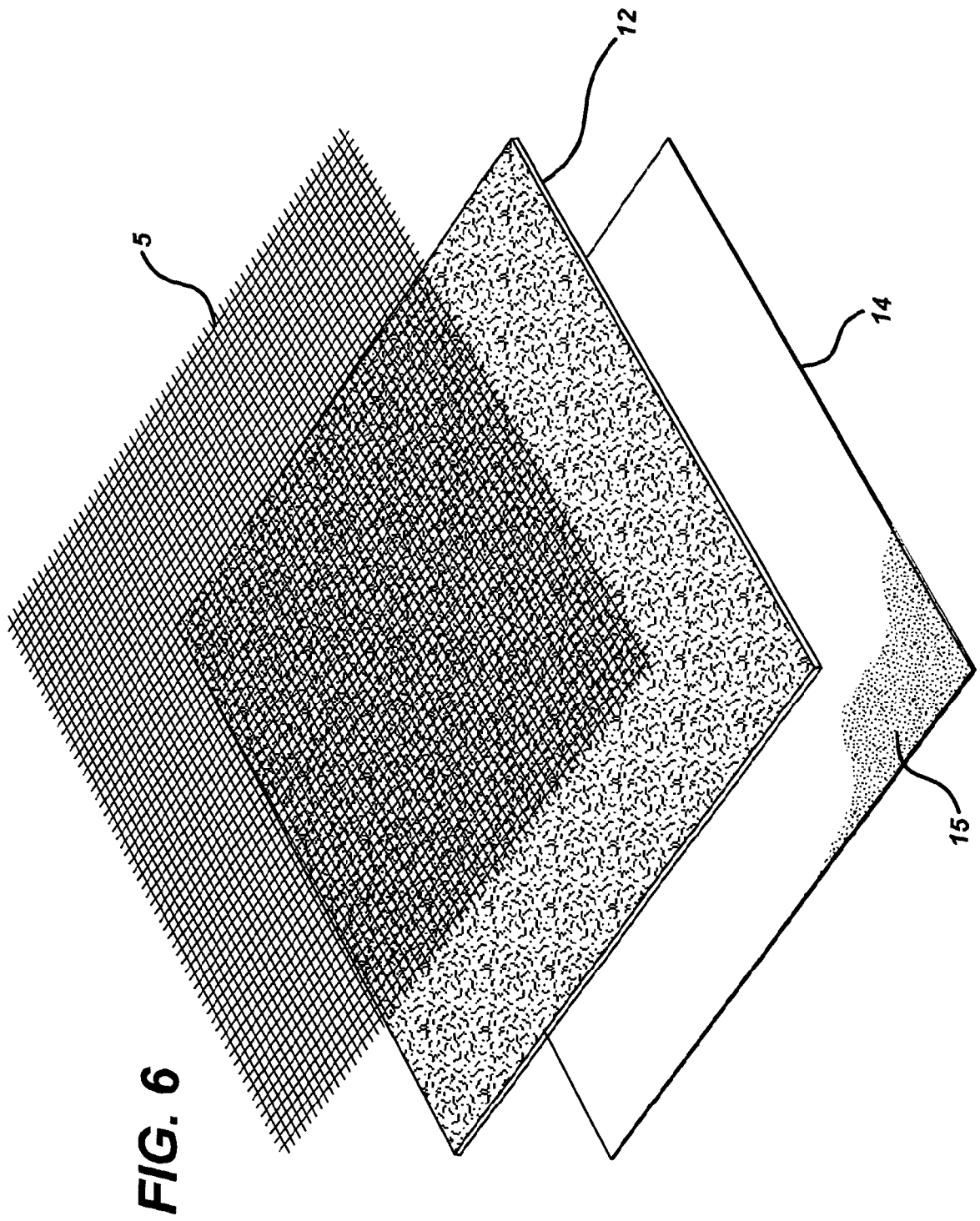
FIG. 6 shows a perspective exploded view of a third product according to the invention.

Referring to FIG. 6, the product according to this embodiment comprises a siliconized substrate gauze 5 as before, but in this embodiment the base layer 12 is a sheet of water-absorbent nonwoven textile, such as a nonwoven viscose web or a nonwoven alginate/nylon web. The absorbent textile 12 can absorb wound fluid and swell in use, while remaining strongly bonded to the siliconized gauze wound contacting layer 5. A backing sheet 14 of semipermeable film coated with adhesive 15 is applied over the opposite surface of the textile layer to prevent leakage of liquid from the back of the dressing.

Figure 7:
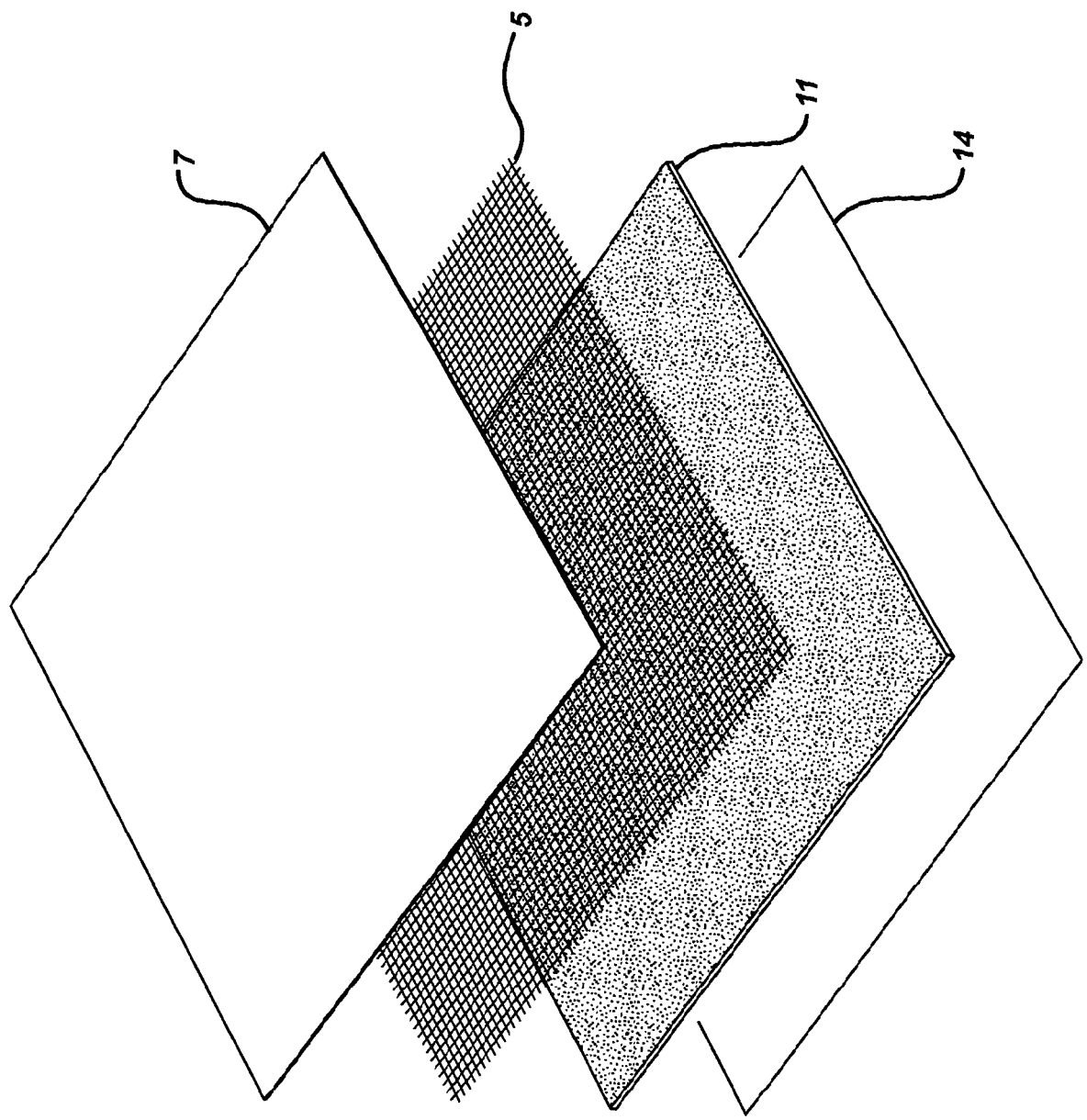
FIG. 7 shows a perspective exploded view of a fourth product according to the invention.
Figure 8:
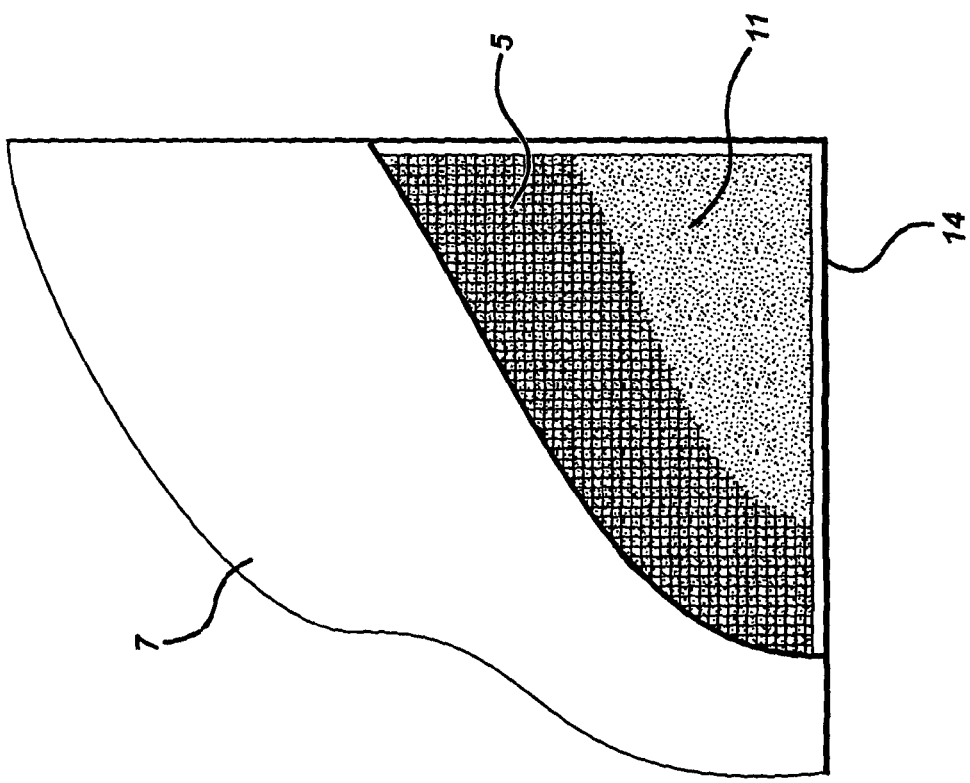
FIG. 8 shows a partially cut away view of part of the product of FIG. 7.

Referring to FIGS. 7 and 8, the product according to this embodiment comprises a siliconized substrate gauze 5 laminated to a hydrophilic foam layer and cover sheet as for the embodiment of FIG. 4. The embodiment of FIGS. 7 and 8 further comprises a backing sheet 14 of adhesive-coated semipermeable film as described for FIG. 6 that is applied over the opposite surface of the foam layer from the siliconized substrate to prevent leakage of liquid through the dressing.

Figure 10:
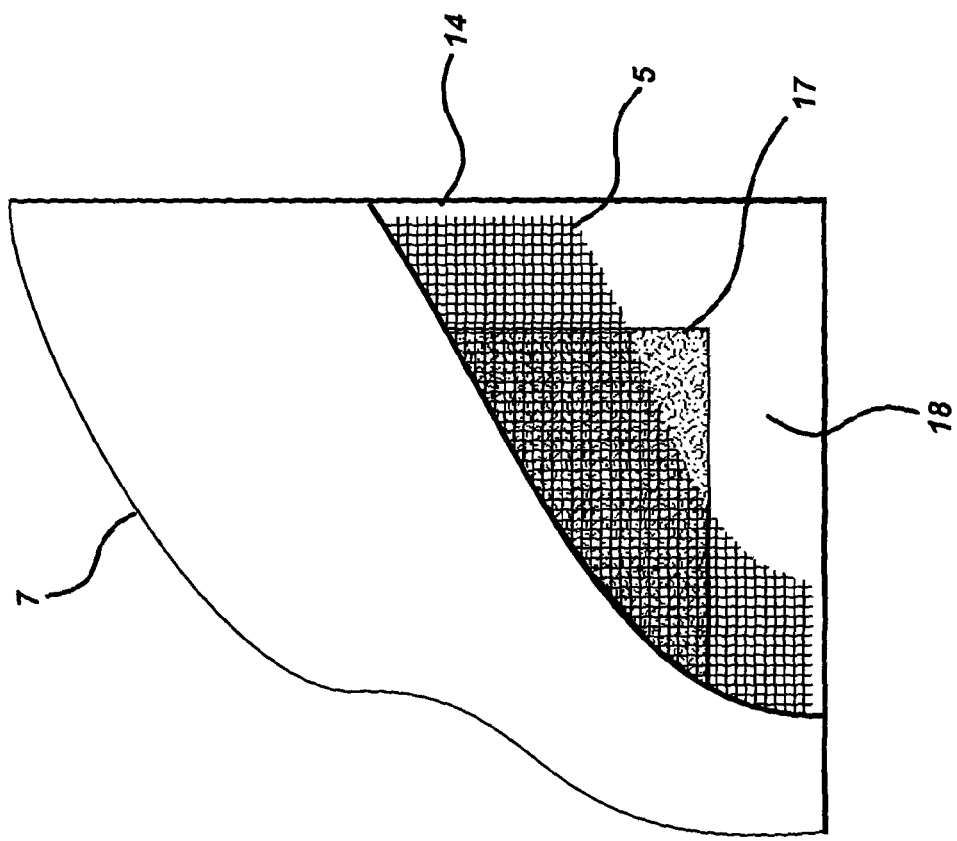
FIG. 10 shows a partially cut away view of part of the product of FIG. 9.
Figure 9:
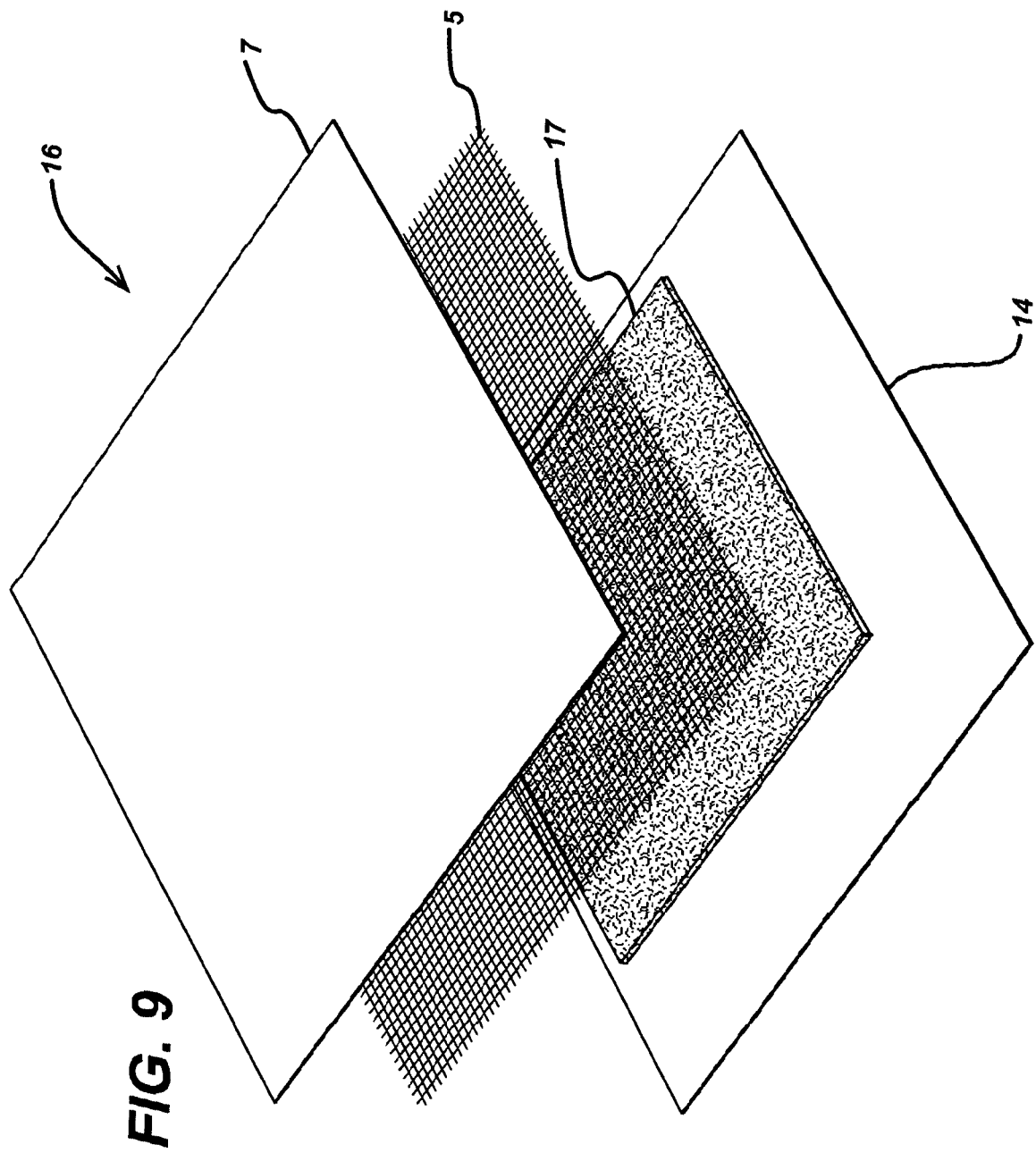
FIG. 9 shows a perspective exploded view of a fifth product according to the invention.

Referring to FIGS. 9 and 10, the product 16 according to this embodiment is an island dressing. It comprises a siliconized substrate gauze 5 laminated to a hydrophilic liquid-absorbent layer of textile material 17 and a polyurethane semipermeable backing sheet 14 as for the embodiment of FIG. 6. A silicone-coated paper release sheet 7 is provided over the wound-facing surface of the gauze 5. However, the area of the textile material 17 is less than that of the gauze 5 or the backing sheet 14, whereby a margin 18 of the backing sheet extends around all edges of the textile material. The siliconized gauze is therefore directly bonded to the backing sheet over the margin, as well as to the wound-facing surface of the textile layer 17. This bonding of the siliconized gauze to the margin 18 of the backing sheet 14 helps to keep the absorbent island in place on the backing sheet, and also provides the margin 18 with a skin-friendly, weakly adherent (tacky) siliconized surface for contact with the skin around a wound. The island dressings are less prone to leakage of wound fluids from the edges of the dressing than the simple laminates described above.

Figure 11:
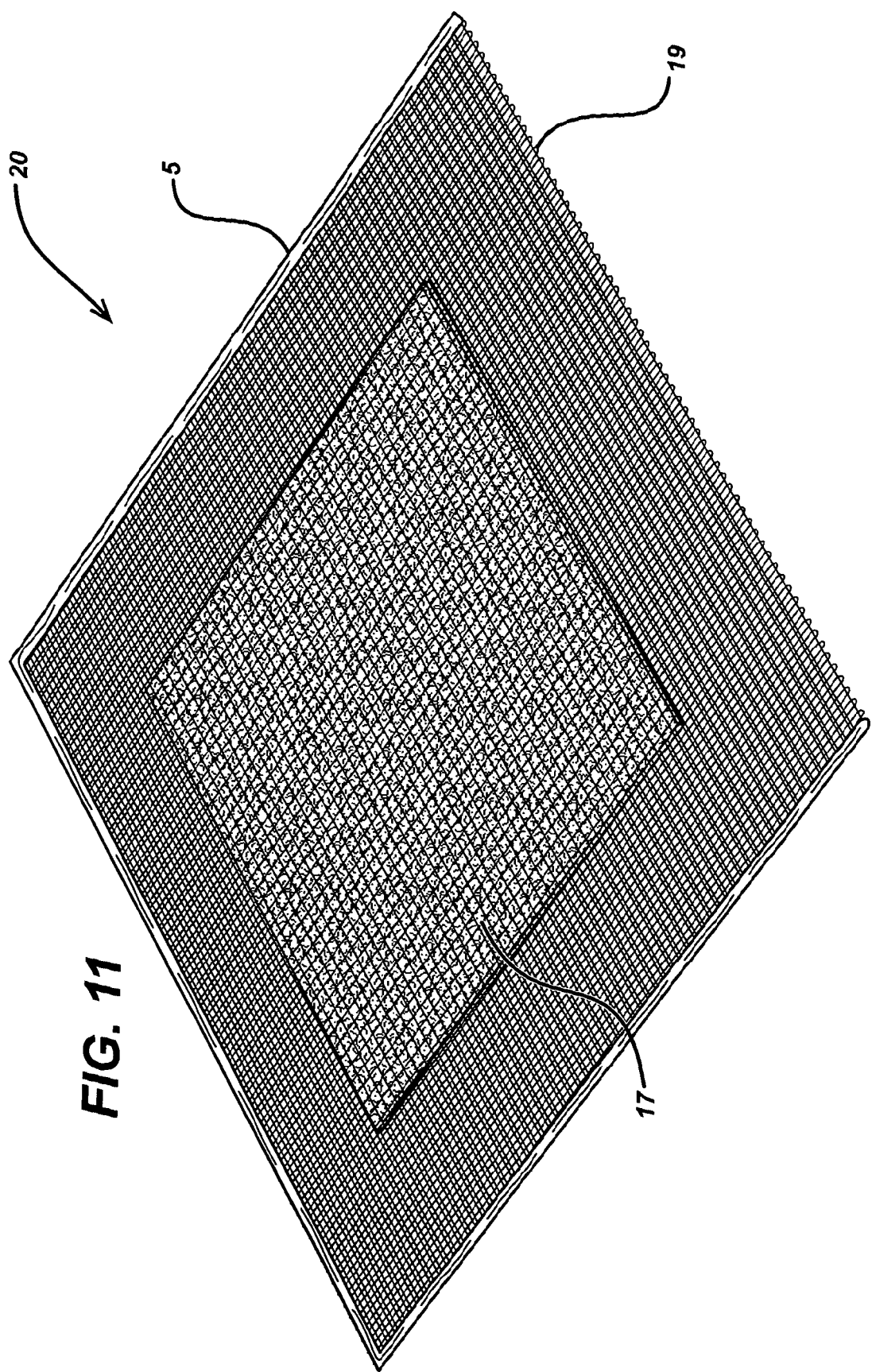
FIG. 11 shows a perspective view of a sixth product according to the invention.

Referring to FIG. 11, the product 20 is an envelope-type dressing formed from upper and lower sheets 5,19 of siliconized gauze, which may be separate sheets or a single sheet folded over. An island 17 of hydrophilic liquid-absorbent textile material is located centrally between the sheets 5,19. The sheets 5,19 are bonded to the island 17 and to each other in the marginal area around the island 17. The resulting envelope can be applied to a wound in either orientation.

Figure 12:
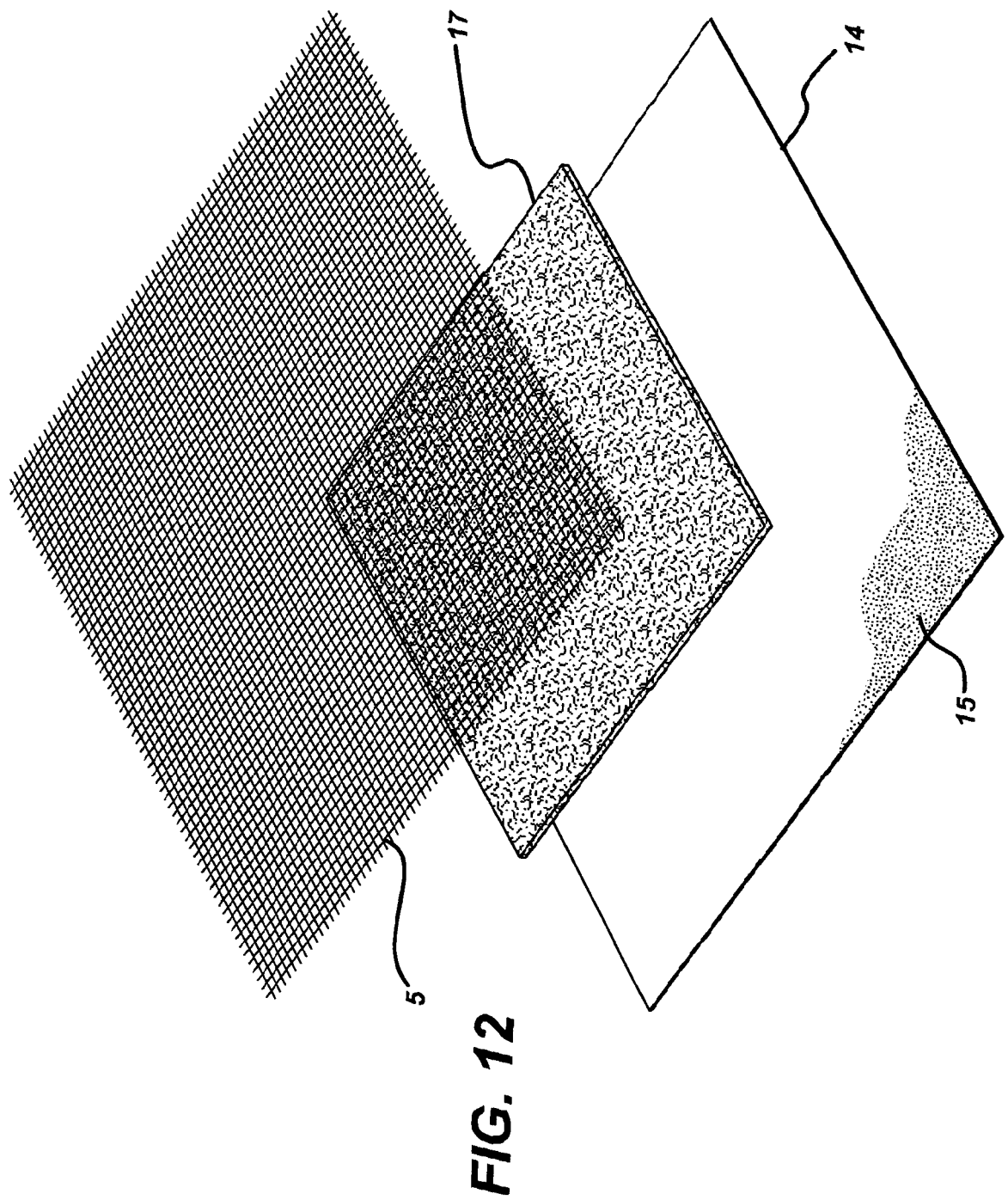
FIG. 12 shows a perspective exploded view of a seventh product according to the invention.
Figure 13:
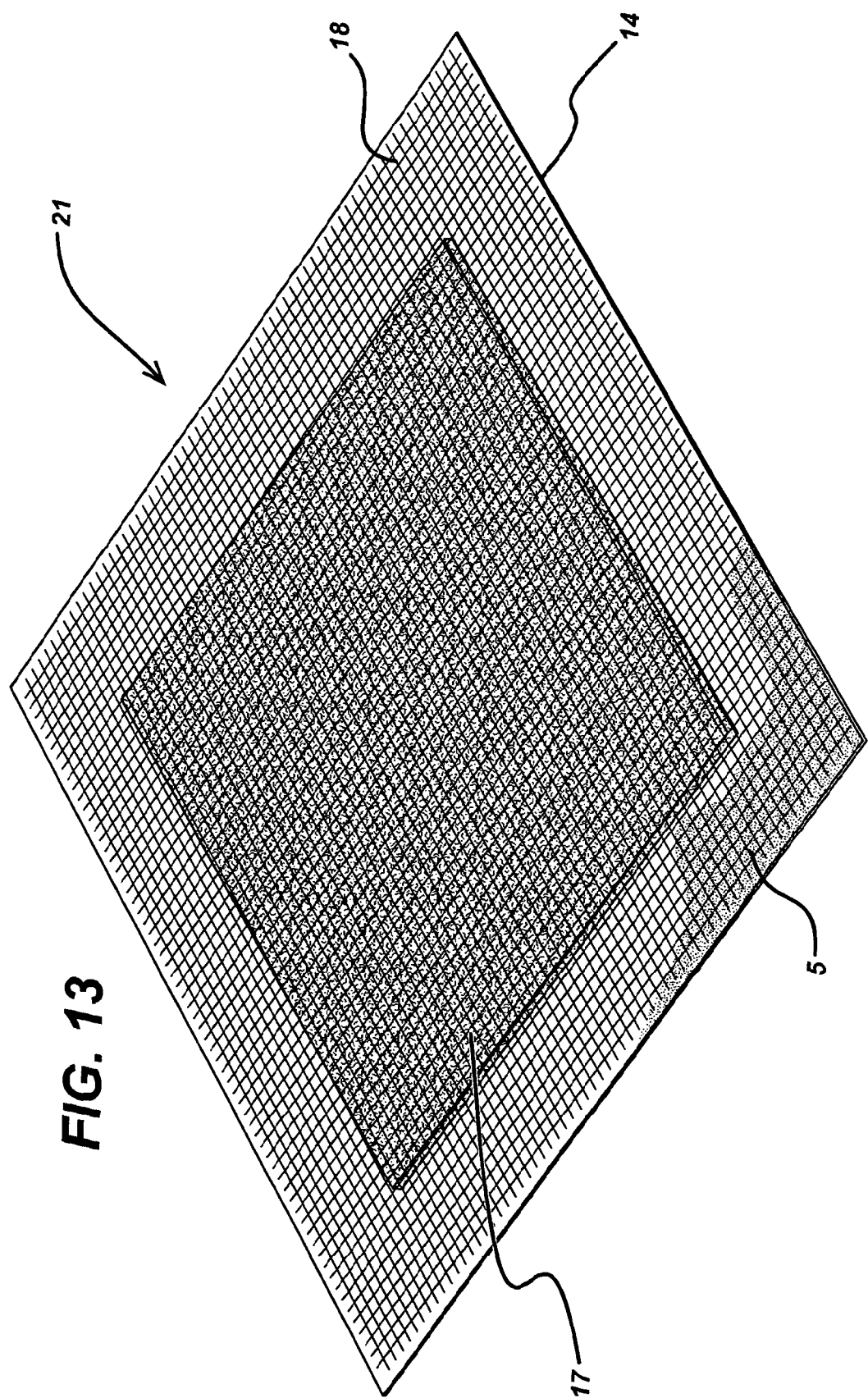
FIG. 13 shows a perspective view of the product of FIG. 12.

Referring to FIGS. 12 and 13, the product 21 according to this embodiment is an island dressing similar to that of FIGS. 9 and 10. It comprises a siliconized substrate gauze 5 laminated to a hydrophilic liquid-absorbent layer of textile material 17 and a polyurethane semipermeable backing sheet 14 as for the embodiment of FIG. 6. A layer of polyurethane pressure-sensitive adhesive 15 is provided over the wound-facing surface of the backing sheet 14. In certain alternative embodiments, the gauze 5 is coterminous with the island 17 so that the margin 18 is solely adhesive-coated to provide adhesion to skin around a wound.

Figure 14:
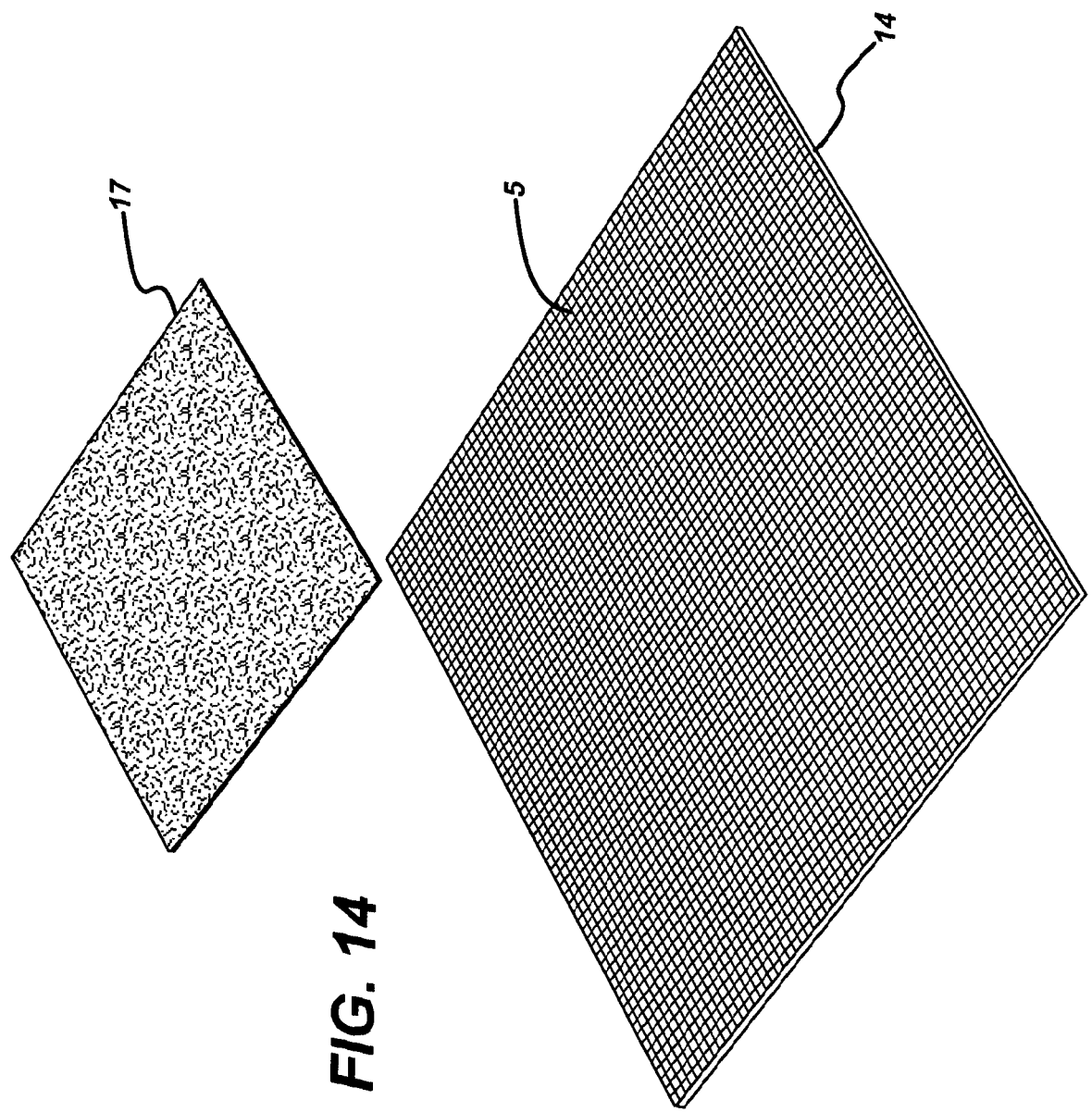
FIG. 14 shows a perspective partially exploded view of an eighth product according to the invention.

Referring to FIG. 14, an alternative island dressing structure is shown wherein the siliconized gauze layer 5 is laminated directly to a semipermeable polyurethane backing sheet 14, and an absorbent island 17 is laminated over and bonded to the gauze layer 5. In these embodiments, the gauze layer 5 acts as a tie layer to bond the absorbent island 17 to the backing sheet. A further siliconized gauze layer (not shown) may be bonded over the top of the absorbent layer, either coterminous with the absorbent layer 17 or coterminous with the backing sheet 14, in similar fashion as for the embodiments of FIG. 9-10 or 12-13.

Figure 15:
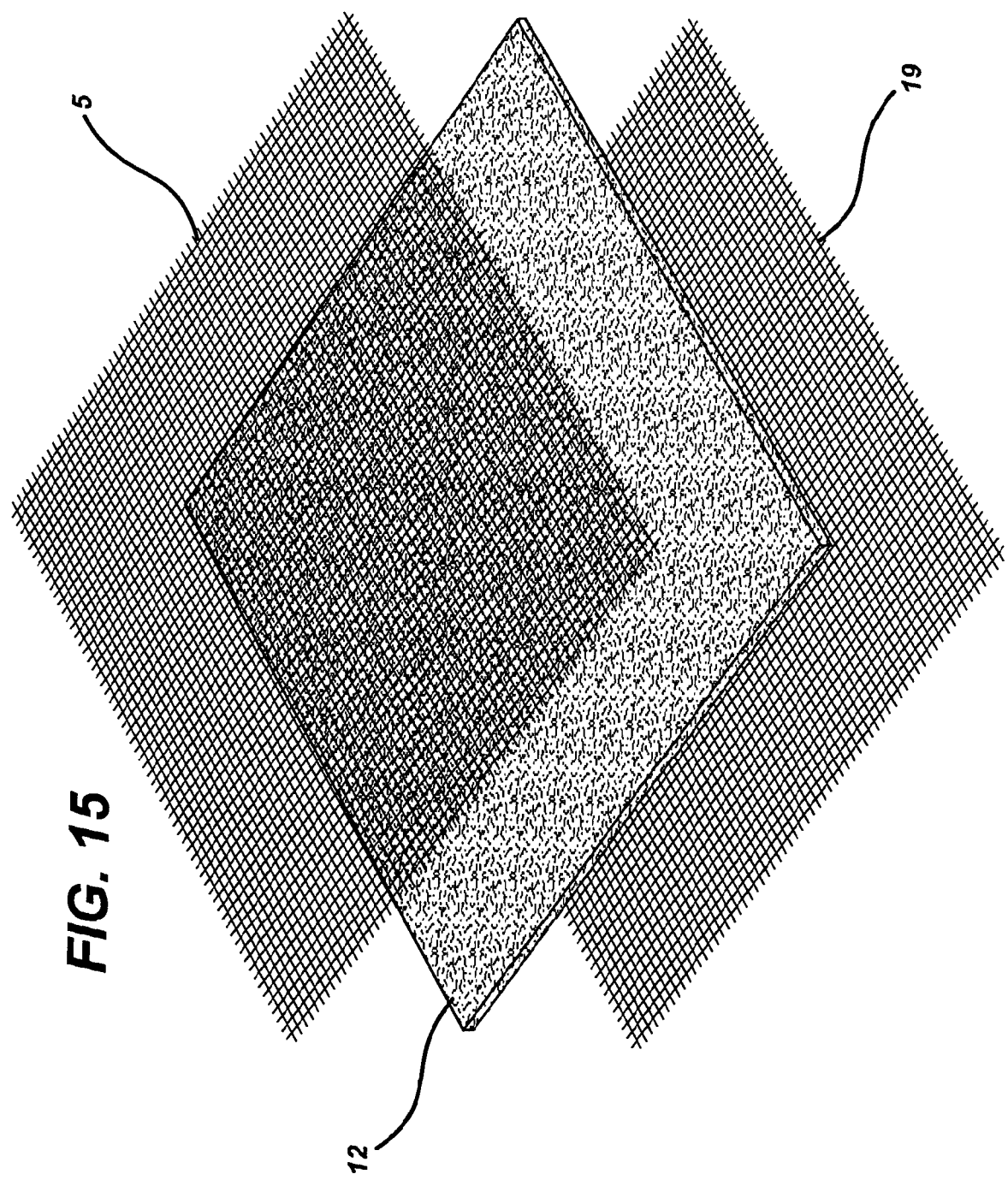
FIG. 15 shows a perspective exploded view of a ninth product according to the invention.
Figure 16:
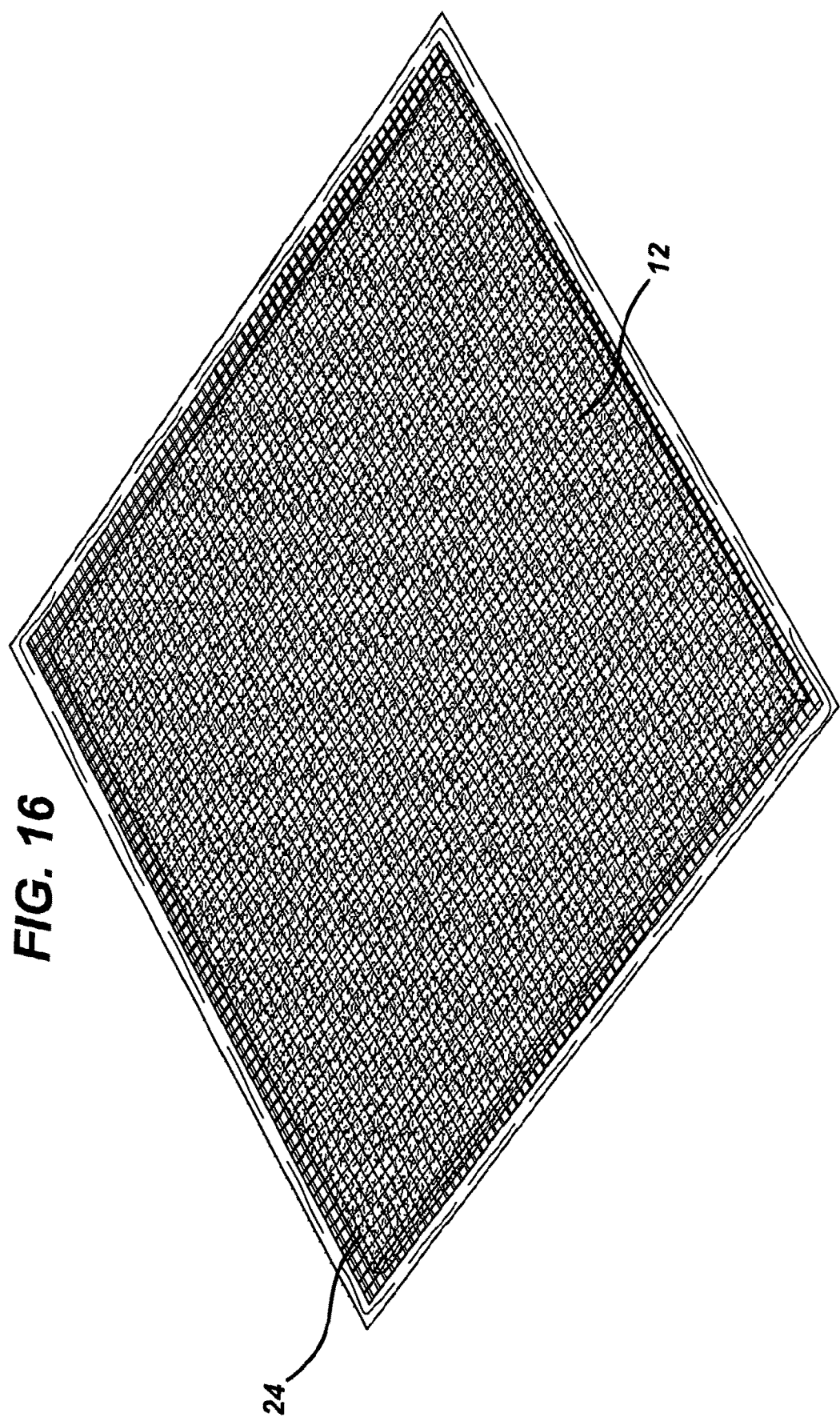
FIG. 16 shows a perspective view of the product of FIG. 15.

Referring to FIGS. 15 and 16, this embodiment is a sandwich structure having upper and lower sheets of siliconized gauze 5,19 sandwiching and bonded to a layer of nonwoven textile absorbent material 12. Suitably, the layers 5,12 and 19 are coterminous, or a small margin 24 of layers 5,19 directly bonded to each other may extend around the edges of the dressing.

The products according to the invention may be made by a process according to the invention. This process starts from a continuous web of cellulose acetate gauze that is passed through a fluid silicone coating composition and nip rollers to coat and impregnate the gauze with the silicone composition. The silicone coating composition is prepared by mixing Components A and B of a soft silicone skin adhesive silicone elastomer kit supplied by Dow Corning under product reference Q7-9177, The components are mixed in weight ratio 50:50. Component A comprises a bis-dimethylvinyl terminated polydimethylsiloxane and a platinum catalyst. Component B comprises a bis-hydride terminated polydimethylsiloxane. To the mixture is added 2-methyl-3-butyn-2-ol inhibitor at a concentration of 0.02 wt. %.

The coated substrate then passes over a blower 17 to open the apertures of the coated substrate that may have been occluded by the silicone.

The coated gauze is then passed through an oven 18 held at 150° C. Typical conditions are 5 passes at 4.2 m/min, total residence time 1.5 minutes. This results in thermal partial cure of the silicone coating. The coated material is then allowed to cool, and the base layer and a release coated paper cover sheet are then continuously applied to the upper and lower surfaces.

The material is then cut and packaged as shown in FIG. 1, followed by gamma irradiation with 35-50 kGy of Cobalt 60 radiation at 7-9 kGy/hr to sterilize the products and complete the cure. The irradiation curing results in a further increase in both hardness and tackiness of the silicone coating, and further bonds the silicone coating strongly to the base layer.

Procedure 1: Measurement of Surface Tackiness by the Loop Tack Test

The tackiness of the silicone coatings produced by the methods of the invention was measured in a tensile tester, such as an Instron tester, using the set-up shown in FIG. 17.

Samples of the coated fully cured gauze laminates were cut to dimensions 5×9.5 cm. Margins of 1 cm were marked out along the long edges by drawing straight lines 1 cm from the long edges. The cover sheets were removed, and the sheet of coated gauze 30 was looped around and the 1 cm margins 30,32 on opposed edges of one surface (opposite the surface being measured) were applied firmly to opposite sides of a 2 mm thick metal spacer bar 34. Strips of polypropylene film 1 cm wide 36,37 were then applied to the opposite surfaces of the coated gauze opposite the spacer bar 34 to prevent the coated gauze from adhering to the jaws of the measurement device.

The assembly of polypropylene strips, coated gauze and spacer bar was then gripped in the jaws 38 of the Instron tester. The loop of coated gauze 40 having the surface under test outermost was then lowered onto a clean polycarbonate surface 42 of dimensions 15.5 cm×3.8 cm so that the loop adheres to the surface, and raised to detach the loop from the surface. Lowering and raising are performed at 300 mm/min, and the minimum distance between the jaws 38 and the polycarbonate surface 42 is 15 mm. The measured tack (in Newtons) is the maximum force measured while detaching the loop from the surface. Average of three measurements was used.

Procedure 2: Measurement of Peel Strength

The peel strength of the laminates produced by the methods of the invention was measured in a tensile tester, such as an Instron tester, using the set-up shown schematically in FIG. 18. The test strip 50 is positioned horizontally with the substrate layer and base layer in respective jaws 52,54 of the tester to give 180 degree peel. The test was performed on strips of laminate of dimensions 25.4 mm×254 mm. The pull rate was 400 mm/minute. The reported peel strength was the average over the length of the strip in grams force (gf), whereby 1 gf=3.86 mN/cm (cm refers to the width of the strip in cm).

EXAMPLE 1

Samples were prepared by the method of the present invention. The first sample comprises a silicone-coated gauze (ADAPTIC TOUCH available from Systagenix Wound Management Manufacturing Ltd., Gargrave, UK) laminated to a polyurethane hydrophilic foam sheet (TIELLE, available from Systagenix Wound Management Manufacturing Ltd., Gargrave, UK).

Peel strength tests on the laminate before and after the final gamma sterilization and crosslinking step are shown in Table 1 below.

TABLE 1

|  | Average Load (gf) |
|---|---|
| TIELLE + TOUCH (separate sterilisation) |  |
| 1 | 5.71 |
| 2 | 4.87 |
| 3 | 4.58 |
| Average | 5.05 |
| TIELLE + TOUCH (sterilised together) |  |
| 1 | 126.36 |
| 2 | 141.45 |
| 3 | 142.90 |
| Average | 136.90 |

It can be seen that the siliconized substrate adheres only weakly to the foam before irradiation, but exhibits strong bonding after irradiation.

EXAMPLE 2

The method of Example 1 was repeated to prepare a laminate of a silicone-coated gauze (ADAPTIC TOUCH available from Systagenix Wound Management Manufacturing Ltd., Gargrave, UK) laminated to a semipermeable wound dressing backing sheet formed of 0.4 mm high-density polyurethane foam of a blocked toluene di-isocyanate nature coated with an aliphatic polyurethane adhesive.

Peel strength tests on the laminate before and after the final gamma sterilization and crosslinking step are shown in Table 2 below. It can be seen that the siliconized substrate adheres only weakly to the foam before irradiation, but exhibits strong bonding after irradiation.

TABLE 2

|  | Average Load (gf) |
|---|---|
| Backing + Substrate (after separate sterilisation) | |
| 1 | 3.44 |
| 2 | 3.94 |
| 3 | too low to register |
| Average | 3.69 |
| Backing + Substrate (sterilised together) | |
| 1 | 84.44 |
| 2 | 73.26 |
| 3 | 95.59 |
| Average | 84.43 |

It can be seen that gamma sterilization of the silicone coated substrate laminated to the base layer results in a very large increase in the bonding strength of the laminate. The siliconized apertured substrate can thus provide a non-adherent wound contacting surface to the polyurethane backing sheet.

EXAMPLE 3

The method of Example 1 was repeated to prepare a laminate of a silicone-coated gauze (ADAPTIC TOUCH available from Systagenix Wound Management Manufacturing Ltd., Gargrave, UK) laminated to second sheet of the same silicone-coated gauze.

Peel strength tests on the laminate before and after the final gamma sterilization and crosslinking step are shown in Table 3 below.

TABLE 3

|  | Average Load (gf) |
|---|---|
| Substrate + Substrate (sterilised separately) | |
| 1 | 13.14 |
| 2 | 15.90 |
| 3 | 21.71 |
| Average | 16.92 |
| Substrate + Substrate (sterilised together) | |
| 1 | 151.19 |
| 2 | 156.12 |
| 3 | 174.84 |

It can be seen that the siliconized substrate adheres only weakly to itself before irradiation, but exhibits strong bonding after irradiation.

EXAMPLE 4

The method of Example 1 was repeated to prepare a laminate of a silicone-coated gauze (ADAPTIC TOUCH® available from Systagenix Wound Management Manufacturing Ltd., Gargrave, UK) laminated to sheet of nonwoven textile (SILVERCEL® available from Systagenix Wound Management Manufacturing Ltd., Gargrave, UK). The textile is a calcium alginate needled felt dressing incorporating metallic-silver-coated nylon fibers. The composition is as follows, by weight: calcium alginate and carboxymethyl cellulose (CMC) fibers 60% and silver coated nylon 40%. The basis weight of the fabric layer is about 150 g/m$^2$, and the uncompressed thickness of the fabric layer is about 2 mm. The total silver content of the fabric is about 8 wt. %.

Peel strength tests on the laminate before and after the final gamma sterilization and crosslinking step are shown in Table 3 below.

TABLE 4

|  | Average Load (gf) |
|---|---|
| Silvercel + substrate (sterilised separately) | |
| 1 | 2.87 |
| 2 | 3.05 |
| Average | 2.96 |
| Silvercel + Substrate (sterilised together) | |
| 1 | 299.18 |
| 2 | 336.4 |
| Average | 317.79 |

It can be seen that the siliconized substrate adheres only weakly to itself before irradiation, but exhibits strong bonding after irradiation. In fact, under the peel test conditions the siliconized substrate does not peel from the surface of the textile, but instead the textile itself peels apart.

The above examples have been described by way of illustration only. Many other embodiments falling within the scope of the accompanying claims will be apparent to the skilled reader.

The invention claimed is:

1. A wound dressing comprising:
an absorbent polyurethane base layer;
an apertured substrate; and
a silicone coating on the apertured substrate;
wherein
the silicone coating on the apertured substrate is covalently bonded to the absorbent polyurethane base layer; and
the silicone coating comprises a bis-dimethylvinyl terminated polydimethylsiloxane and a bis-hydride terminated polydimethylsiloxane.

2. The wound dressing according to claim 1, wherein the absorbent polyurethane base layer is further laminated to an adhesive-coated liquid-impermeable backing sheet.

3. The wound dressing according to claim 2, wherein the wound dressing is in the form of an island dressing wherein the adhesive-coated liquid-impermeable backing sheet is larger than the absorbent polyurethane base layer whereby a margin of the backing sheet extends around one or more edges of the absorbent polyurethane base layer.

4. The wound dressing according to claim 1, wherein a peel strength greater than 200 mN/cm is required to separate the silicone coated apertured substrate from the absorbent polyurethane base layer.

5. The wound dressing according to claim 1, wherein the absorbent polyurethane base layer is in the form of a polymeric film sheet, a foam, a sponge, or a film.

6. The wound dressing according to claim 1, wherein the absorbent polyurethane base layer to which the silicone coating is bonded is hydrophilic.

7. The wound dressing according to claim 1, wherein the absorbent polyurethane base layer is a semipermeable polyurethane film or a hydrophilic polyurethane foam sheet.

8. The wound dressing according to claim 1, wherein the apertured substrate is coated on both sides with the silicone coating, and a surface of the silicone coating opposite the absorbent polyurethane base layer is non-adherent or tacky.

9. The wound dressing according to claim 1, wherein the wound dressing is sterile and is packaged in a microorganism-impermeable container.

10. A wound dressing of claim 1 obtainable by a method comprising the steps of:
providing the apertured substrate layer;
coating the substrate layer with a fluid silicone prepolymer composition; thermally partially curing said silicone prepolymer composition to form a partially cured silicone coating on the substrate;
laminating the coated substrate layer to the base layer to form a laminate having said partially cured silicone coating in contact with a surface of the base layer; and
exposing the laminate to ionizing radiation, to further cure the partially cured silicone coating and to bond the silicone coating to said surface of the base layer.

11. The wound dressing of claim 1, wherein the silicone coating is coated on a first side and a second side of the apertured substrate, wherein the first side of the apertured substrate is adapted to be bonded to the surface of the absorbent polyurethane base layer, and wherein the second side of the apertured substrate coated with the silicone coating is substantially non-adherent.

12. The wound dressing of claim 1, wherein the apertured substrate comprises a cellulose acetate gauze.

13. The wound dressing of claim 1, wherein the wound dressing is sterilized by ionizing radiation.

* * * * *